(12) United States Patent
Dahl et al.

(10) Patent No.: US 12,108,213 B2
(45) Date of Patent: Oct. 1, 2024

(54) SELF-CHECK PROTOCOL FOR USE BY EAR-WEARABLE ELECTRONIC DEVICES

(71) Applicant: STARKEY LABORATORIES, INC., Eden Prairie, MN (US)

(72) Inventors: Brian Dahl, Minnetrista, MN (US); Zac Jensen, Norwood Young America, MN (US); Joshua Braband, Minneapolis, MN (US); Denise Klokow, Faribault, MN (US); Brantly Sturgeon, Burnsville, MN (US); Jaymin Baroda, Eden Prairie, MN (US)

(73) Assignee: STARKEY LABORATORIES, INC., Eden Prairie, MN (US)

( * ) Notice: Subject to any disclaimer, the term of this patent is extended or adjusted under 35 U.S.C. 154(b) by 207 days.

(21) Appl. No.: 17/834,306

(22) Filed: Jun. 7, 2022

(65) Prior Publication Data
US 2022/0408199 A1 Dec. 22, 2022

Related U.S. Application Data

(60) Provisional application No. 63/212,244, filed on Jun. 18, 2021.

(51) Int. Cl.
*H04R 25/00* (2006.01)
*A61B 5/00* (2006.01)
(Continued)

(52) U.S. Cl.
CPC ......... *H04R 25/305* (2013.01); *A61B 5/0059* (2013.01); *A61B 5/6815* (2013.01);
(Continued)

(58) Field of Classification Search
None
See application file for complete search history.

(56) References Cited

U.S. PATENT DOCUMENTS

| 7,003,128 B2 | 2/2006 | Boonen |
| 7,242,778 B2 | 7/2007 | Csermak et al. |
| | (Continued) | |

FOREIGN PATENT DOCUMENTS

| EP | 3905721 A1 * | 11/2021 | ........... H04R 1/1025 |
| WO | WO-2020042498 A1 * | 3/2020 | ........... H04R 1/1016 |

OTHER PUBLICATIONS

Earwax in AirPods, or a Fault? New Apple Tool will Find Out., Ben Lovejoy, Oct. 22, 2020 (7 pages).

*Primary Examiner* — Qin Zhu
(74) *Attorney, Agent, or Firm* — Mueting Raasch Group

(57) ABSTRACT

An ear-wearable electronic device includes one or more processors configured to detect presence of first and second hearing devices in a charging case, and to initiate a self-check protocol by at least one of the first and second hearing devices. The self-check protocol comprises wirelessly coupling the first and second hearing devices, selectively activating at least one electronic component of the first hearing device, and assessing performance of the second hearing device using an output or a response of the at least one electronic component of the first hearing device. The self-check protocol also comprises selectively activating at least one electronic component of the second hearing device, assessing performance of the first hearing device using an output or a response of the at least one electronic component of the second device, and storing results of the performance assessment in a memory.

24 Claims, 22 Drawing Sheets

(51) Int. Cl.
*G01J 1/44* (2006.01)
*G01K 15/00* (2006.01)
*H01Q 1/27* (2006.01)
*H02J 7/00* (2006.01)
*H04R 1/10* (2006.01)
*H04R 29/00* (2006.01)

(52) U.S. Cl.
CPC .......... *H02J 7/0044* (2013.01); *H04R 25/554* (2013.01); *H04R 25/604* (2013.01); *H04R 25/609* (2019.05); *G01J 1/44* (2013.01); *G01J 2001/444* (2013.01); *G01K 15/005* (2013.01); *H01Q 1/273* (2013.01); *H04R 2225/31* (2013.01); *H04R 2225/51* (2013.01)

(56) References Cited

U.S. PATENT DOCUMENTS

| | | |
|---|---|---|
| 8,249,262 B2 | 8/2012 | Chua et al. |
| 9,014,405 B2 | 4/2015 | Larsen et al. |
| 10,687,151 B2 | 6/2020 | Petersen et al. |
| 10,904,674 B2 | 1/2021 | Goldstein |
| 2007/0286429 A1 | 12/2007 | Grafenberg et al. |
| 2010/0272273 A1* | 10/2010 | Chua .................... H04R 1/1066 381/60 |
| 2014/0146974 A1* | 5/2014 | Krueger ................ H04R 25/30 381/60 |
| 2019/0069096 A1* | 2/2019 | Petersen ............. H04R 25/604 |

\* cited by examiner

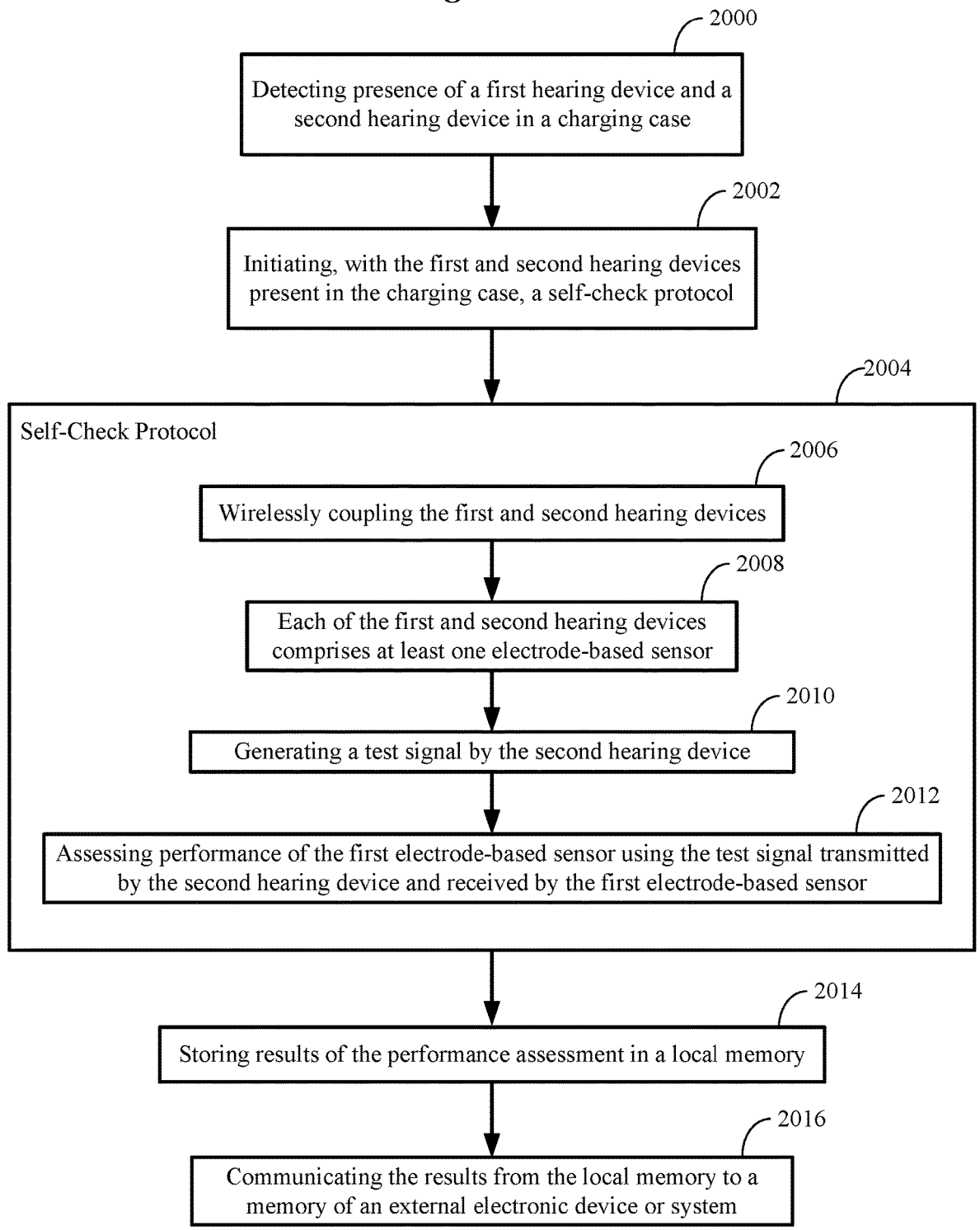

SELF-CHECK PROTOCOL FOR USE BY EAR-WEARABLE ELECTRONIC DEVICES

RELATED APPLICATIONS

This application claims the benefit of U.S. Provisional Application No. 63/212,244, filed Jun. 18, 2021, the content of which is hereby incorporated herein by reference.

TECHNICAL FIELD

This application relates generally to ear-level electronic systems and devices, including hearing devices, personal sound amplification devices, hearing aids, hearables, physiologic monitoring devices, biometric devices, position and/or motion sensing devices, and other ear-wearable electronic devices.

SUMMARY

Some embodiments are directed to a method comprising detecting presence of a first hearing device and a second hearing device in a charging case, and initiating, with the first and second hearing devices present in the charging case, a self-check protocol by at least one of the first and second hearing devices. The self-check protocol comprises wirelessly coupling the first and second hearing devices, selectively activating at least one electronic component of the first hearing device, and assessing performance of the second hearing device using an output or a response of the at least one electronic component of the first hearing device. The method also comprises selectively activating at least one electronic component of the second hearing device, assessing performance of the first hearing device using an output or a response of the at least one electronic component of the second device, and storing results of the performance assessment in a memory.

Some embodiments are directed to an ear-wearable electronic device comprising one or more processors operatively coupled to a memory. The one or more processors are configured to detect presence of a first hearing device and a second hearing device in a charging case, and initiate, with the first and second hearing devices present in the charging case, a self-check protocol by at least one of the first and second hearing devices. The self-check protocol implemented by the one or more processors comprises wirelessly coupling the first and second hearing devices, selectively activating at least one electronic component of the first hearing device, and assessing performance of the second hearing device using an output or a response of the at least one electronic component of the first hearing device. The self-check protocol implemented by the one or more processors also comprises selectively activating at least one electronic component of the second hearing device, assessing performance of the first hearing device using an output or a response of the at least one electronic component of the second device, and storing results of the performance assessment in the memory.

Some embodiments are directed to a method comprising initiating, with first and second hearing devices positioned in a charging case, a self-check protocol by at least one of the first and second hearing devices. The self-check protocol comprises wirelessly coupling the first and second hearing devices, and activating a first microphone of the first hearing device and generating an acoustic test stimulus by a second acoustic transducer of the second hearing device. The method also comprises assessing performance of the first microphone in response to the acoustic test stimulus by comparing a response of the first microphone to a pre-established profile representative of nominal microphone performance and detecting sub-optimal performance of the first microphone in response to measuring a specified deviation from the pre-established profile. The method comprises activating a second microphone of the second hearing device and generating an acoustic test stimulus by a first acoustic transducer of the first hearing device. The method also comprises assessing performance of the second microphone in response to the acoustic test stimulus by comparing a response of the second microphone to the pre-established profile and detecting sub-optimal performance of the second microphone in response to measuring a specified deviation from the pre-established profile. The method also comprises storing results of the performance assessment in a memory, such as a memory of the first and/or second hearing devices.

Some embodiments are directed to ear-wearable electronic devices configured to facilitate performance of a self-check protocol within a charging case. The devices comprise a first hearing device and a second hearing device each comprising a microphone, an acoustic transducer, a communication device, and a controller coupled to memory. The controller of at least one of the first and second hearing devices is configured to activate a first microphone of the first hearing device and generate an acoustic test stimulus by a second acoustic transducer of the second hearing device. The controller is configured to assess performance of the first microphone in response to the acoustic test stimulus by comparing a response of the first microphone to a pre-established profile representative of nominal microphone performance and detecting sub-optimal performance of the first microphone in response to measuring a specified deviation from the pre-established profile. The controller is also configured to activate a second microphone of the second hearing device and generate an acoustic test stimulus by a first acoustic transducer of the first hearing device. The controller is configured to assess performance of the second microphone in response to the acoustic test stimulus by comparing a response of the second microphone to the pre-established profile and detecting sub-optimal performance of the second microphone in response to measuring a specified deviation from the pre-established profile. The controller is also configured to store results of the performance assessment in a memory, such as a memory of the first and/or second hearing devices.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings wherein:

FIG. 20 illustrates a Self-Check protocol in accordance with any of the embodiments disclosed herein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1A:
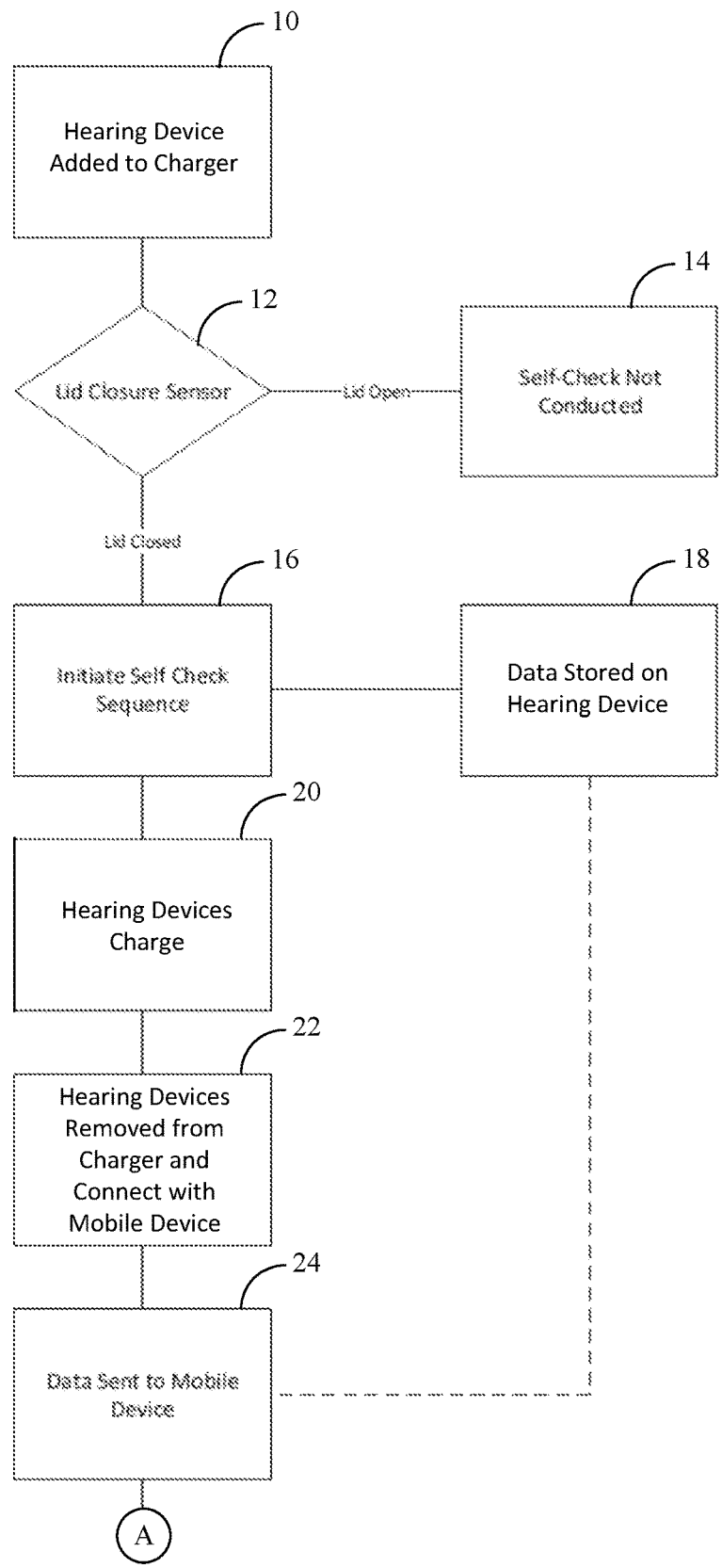
FIGS. 1A-1C illustrate a method which includes a Self-Check protocol in accordance with any of the embodiments disclosed herein.

Embodiments of the disclosure are directed to ear-wearable electronic devices configured to implement a Self-Check protocol alone or in cooperation with an external electronic device. Embodiments of the disclosure are directed to ear-wearable electronic devices configured to implement a Self-Check protocol when situated in a closeable charging case.

Currently, hearing aids and other ear-wearable electronic devices are tested at the end of the manufacturing line. At this stage, the hearing aid or ear-wearable electronic devices is, essentially, in its 'best performance state'. Once introduced into the field, a hearing aid, for example, is subjected to numerous stress events that will degrade its performance. Some of these stress events include, but are not limited to, being subjected to foreign material (e.g., wax, body oil), environmental conditions (e.g., rain, dust, pollutants, etc.), and mechanical stress events (e.g., normal wear, excessive wear, excursion cases). Throughout this entire user experience, there are limited feedback paths to the wearer of a hearing aid or other ear-wearable electronic device to inform the wearer of the health of their device. If the device performance is indeed degraded, the wearer is presently not provided with improvement pathways.

Over the life of hearing aids and other ear-wearable electronic devices, device performance will degrade and, presently, the wearer is the primary feedback loop to determine if the performance has degraded to a degree which requires professional assistance or intervention. Typically, this takes the form of setting up an appointment with an audiologist or hearing device professional which results in some delay between the request for service/assistance and the appointment. From there, the audiologist or hearing device professional will conduct rudimentary analysis to determine if he or she can remedy the degradation of the hearing device. In cases where the audiologist or hearing device professional cannot sufficiently remedy the hearing device performance problem, the wearer will typically return the device to the manufacturer for warranty repair.

Throughout this cycle, the key problem is that there is little, if any, quantifiable data from which regular diagnoses of the hearing device's health can be made to assess the health of the hearing device (presently, the industry is reliant on the wearer to determine device health). Furthermore, due to 'failure based' trigger modes of operation, opportunities for preventive care, that otherwise could have recovered the hearing device, are not possible. These preventive care options could include cleaning the hearing device or replacing serviceable components.

Embodiments of the disclosure are directed to hardware and methods for conducting regular measurements in situ of a hearing device charger (e.g., a charging case). The measurements made in situ a hearing device charger can include one or more of acoustic, electrical, optical, thermal, and mechanical measurements. These measurements can be compared against nominal performance information and any deviations can be recorded. If significant deviations occur, the hearing device system can initiate prescriptive actions, such as generating wearer instructions to clean or replace components, and manually or automatically sending data to the manufacturer or hearing device professional for analysis or even replacement of the device without the wearer being aware of the fault (e.g., a replacement hearing device is delivered to the wearer's door step the day before the hearing device is expected to cease operation).

A hearing device system (e.g., one or two ear-wearable electronic hearing devices and a charging case) of the present disclosure can be configured to provide automatic, daily measurements (e.g., acoustic, electrical, optical, thermal, and mechanical) to evaluate hearing device performance. A hearing device system of the present disclosure can be configured to determine if a particular component or sensor (e.g., receiver/speaker, microphone, transceiver, physiologic sensor, inertial measurement unit, temperature sensor) is operating sub-optimally (e.g., failing). Measurements made by the hearing device system can be compared against known component and/or sensor performance profiles (e.g., known acoustic profiles) as indicators for failure modes. A hearing device system of the present disclosure can be configured to prescribe preventive care before hearing device performance has degraded to the point that the wearer becomes aware of the performance degradation. Measurement data produced by the hearing device system can be provided to hearing device professionals, retailers, and manufacturers via the cloud (e.g., via the Internet).

Embodiments of the disclosure are directed to a Self-Check protocol in which hearing device hardware and embedded software are used to triangulate the health of hearing devices after being placed in a charging unit or case (also referred to herein as a charger). For example, a pair of hearing devices (e.g., hearing aids or other hearables) is placed into a charger having a lid for daily charging. Closing of the charger lid provides a significant reduction in ambient noise and increases accuracy of various types of measurements (e.g., acoustic, optical, thermal measurements). The hearing devices are configured to detect when they enter a charging mode through hearing device firmware.

A Self-Check protocol of the present disclosure is built into the hearing device (e.g., as programmed instructions stored in memory and readable by a logic device or processor of the hearing device). The Self-Check protocol utilizes components and/or sensors of the hearing device (e.g., receivers, speakers, microphones) combined with test stimuli (e.g., a multi-tone or continuous sweep tone stimulus) to evaluate hearing device performance. Results of the Self-Check protocol can be stored in the hearing device and/or the charger until the device and/or charger connects with an external electronic device (e.g., the wearer's smartphone, mobile phone, tablet, laptop, wireless access point). The results can be uploaded to a cloud application wherein mitigation steps can be taken (e.g., by the hearing device professional, audiologist, retailer, manufacturer) if the results are unacceptable. The Self-Check protocol can be implemented at least once per 24-hour day. The Self-Check protocol can be implemented during charging of the hearing devices, during pauses in charging or during periods of no charging.

Embodiments of the disclosure are directed to a Self-Check protocol which can be performed on a repeated basis (e.g., daily, weekly, monthly) and over a relatively long time frame (e.g., months, years). Self-Check protocol data stored over time by the hearing device can be analyzed by the hearing device or an external device (e.g., a smartphone, a cloud processor). Changes in the performance of components, transducers, and/or sensors of the hearing device can be monitored by the hearing device or external device to track and/or predict component, transducer and/or sensor performance and failure.

For example, a measured response of a hearing device component, transducer or sensor can be compared against a pre-established performance profile (e.g., performance specification). The measured response and comparison data can be saved in the hearing device and analyzed against previous measured responses that have been measured. Using the measured response and comparison data saved in the hearing device, the Self-Check protocol can monitor and predict when a component, transducer or sensor may fall outside of an identified specification or fail. This information can then be used to alert the user, professional, or manufacturer to preemptively plan or take action to ensure continued hearing device life or minimize device downtime.

A performance trajectory of a given component, transducer or sensor can be computed by a processor of the hearing device, such as by use of a curve fitting algorithm or by use of artificial intelligence or machine learning techniques. Each time the Self-Check protocol is executed, the computed performance trajectory is updated using the prior performance data and the currently acquired performance data. This performance trajectory can be compared to one or more pre-established performance metrics, such as a manufacture's performance profile (e.g., acoustic profile, sensor response profile) or specification. Performance degradation can be calculated and extrapolated, for example, using the performance trajectory data to determine when, in the future, the performance trajectory will fall below a sub-optimal level of performance (e.g., fail).

As discussed previously, preventative action can be taken by the user, professional, or manufacturer to preempt the component, transducer, or sensor from reaching a sub-optimal level of performance. For example, performance of a microphone can be analyzed by the hearing device over time to determine if its response falls within an acceptable range when compared to the manufacturer's pre-established response profile. If, after repeated Self-Check testing, the microphone's performance is predicted to reach a sub-optimal level within six months, for example, the user, professional, or manufacturer can be notified that the microphone should be replaced within the next two or three months. It is noted that any of the components, transducers, and sensors of the hearing device disclosed herein can be subject to performance monitoring and analysis (e.g., performance degradation analysis and trending) and expected/end of life prediction.

Embodiments of the disclosure provide a number of advantages, including eliminating the requirement that the wearer enable and execute a self check operation. This can eliminate the uncertainty of using a separate test device (e.g., the charger itself) to determine the health of the hearing device. Another advantage is the ability to provide remedial or treatment information automatically for the hearing device to implement or for the wearer to provide maintenance.

Embodiments of the disclosure are defined in the Examples. However, below there is provided a non-exhaustive listing of non-limiting examples. Any one or more of the features of these examples may be combined with any one or more features of another example, embodiment, or aspect described herein.

Embodiments of the disclosure are defined in the claims. However, below there is provided a non-exhaustive listing of non-limiting examples. Any one or more of the features of these examples may be combined with any one or more features of another example, embodiment, or aspect described herein.

Example Ex1. A method comprises detecting presence of a first ear-wearable electronic device (e.g., a hearing device, a physiologic monitoring device) and a second ear-wearable electronic device (e.g., a hearing device, a physiologic monitoring device) in a charging case, and initiating, with the first and second hearing devices present in the charging case, a self-check protocol by at least one of the first and second hearing devices. The self-check protocol comprises wirelessly coupling the first and second hearing devices, selectively activating at least one electronic component of the first hearing device, assessing performance of the second hearing device using an output or a response of the at least one electronic component of the first hearing device, selectively activating at least one electronic component of the second hearing device, assessing performance of the first hearing device using an output or a response of the at least one electronic component of the second device, and storing results of the performance assessment in a memory.

Example Ex2. A method comprises detecting presence of a first ear-wearable electronic device (e.g., a hearing device, a physiologic monitoring device) and a second ear-wearable electronic device (e.g., a hearing device, a physiologic monitoring device) in a charging case, and initiating, with the first and second hearing devices present in the charging case, a self-check protocol by at least one of the first and second hearing devices. The self-check protocol comprising wirelessly coupling the first and second hearing devices, selectively activating at least one electronic component of one or both of the first and second hearing devices, assessing performance of one or both of the first and second hearing devices using an output or a response of the at least one electronic component, and storing results of the performance assessment in a memory.

Example Ex3. A method comprises detecting presence of a first ear-wearable electronic device (e.g., a hearing device, a physiologic monitoring device) and a second ear-wearable electronic device (e.g., a hearing device, a physiologic monitoring device) in a charging case, and initiating, with the first and second hearing devices present in the charging case, a self-check protocol. The self-check protocol comprises wirelessly coupling the first and second hearing devices, selectively activating at least one electronic component of each of the first and second hearing devices, assessing performance of the first and second hearing devices using an output or a response of the at least one electronic component, and storing results of the performance assessment in a memory.

Example Ex4. The method according to one or more of Ex1 to Ex3, wherein the at least one component of the first hearing device is the same as the at least one component of the second hearing device.

Example Ex5. The method according to one or more of Ex1 to Ex3, wherein the at least one component of the first hearing device differs from the at least one component of the second hearing device.

Example Ex6. The method according to one or more of Ex1 to Ex5, wherein storing results comprises communicating the results from the memory to an external electronic device or system communicatively coupled to one or both of the charging case and at least one of the first and second hearing devices.

Example Ex7. The method according to Ex6, wherein the external electronic device or system comprises one or more of a personal digital assistance, a smartphone, a tablet, a laptop, a PC, a wireless access point, a cloud server, and an Internet server.

Example Ex8. The method according to one or more of Ex1 to Ex7, wherein storing results comprises storing results of the performance assessment in a memory of one or both of the first and second hearing devices.

Example Ex9. The method according to one or more of Ex1 to Ex8, wherein storing results comprises storing results of the performance assessment in a memory of the charging case.

Example Ex10. The method according to one or more of Ex1 to Ex9, wherein detecting presence comprises detecting closure of a lid of the charging case within which the first and second hearing devices are disposed, and initiating the self-check protocol comprises initiating the self-check protocol after detecting closure of the lid.

Example Ex11. The method according to one or more of Ex1 to Ex10, wherein the self-check protocol comprises determining a first performance metric of the first hearing device, determining a second performance metric of the second hearing device, and assessing performance of the first and second hearing devices comprises determining a relative offset between the first and second performance metrics.

Example Ex12. The method according to one or more of Ex1 to Ex11, wherein selectively activating comprises activating a first electronic component of the first hearing device and activating a second electronic component of the second hearing device, and assessing comprises assessing performance of the first hearing device using an output or a response of the second component, and assessing performance of the second hearing device using an output or a response of the first component.

Example Ex13. The method according to one or more of Ex1 to Ex12, wherein the first hearing device comprises a plurality of first hardware components and the second hearing device comprises a plurality of second hardware components. The method comprises selectively activating comprises activating selected ones of the plurality of the first hardware components and activating selected ones of the plurality of second hardware components. Assessing comprises one or both of assessing performance of the first hearing device using an output or a response of the activated second components, and assessing performance of the second hearing device using an output or a response of the activated first components.

Example Ex14. The method according to one or more of Ex1 to Ex13, wherein the first hearing device comprises a plurality of first hardware components C1 through CN1, where N1 is an integer greater than 2, the second hearing device comprises a plurality of second hardware components C2 through CN2, where N2 is an integer greater than 2, activating comprises selectively activating different combinations of C1, CN1, C2, CN2, and assessing comprises assessing performance of the first and second hearing devices by determining which, if any, of C1, CN1, C2, CN2 is performing sub-optimally in response to selective activation of different combinations of C1, CN1, C2, CN2.

Example Ex15. The method according to one or more of Ex1 to Ex14, wherein one or more of the hardware components comprise one or more electronic components and a PCB supporting or coupled to the one or more electronic components.

Example Ex16. The method according to one or more of Ex1 to Ex15, wherein the one or more hardware components comprise one or more of an electrical component, a logic component, an electromechanical component, a mechanical component, a thermal component, an optical component, and an electro-optical component.

Example Ex17. The method according to one or more of Ex1 to Ex16, wherein the one or more hardware components comprise one or both of a passive hardware component and an active hardware component.

Example Ex18. The method according to one or more of Ex1 to Ex17, wherein the one or more hardware components comprise one or more of a processor, a logic device, a memory, a power source, a radio, a transceiver, a microphone, an acoustic transducer, a user interface, an antenna, a telecoil, and NFMI device, a PCBA, electrical circuitry, electronic circuitry, and optoelectronic circuitry.

Example Ex19. The method according to one or more of Ex1 to Ex18, wherein one or more of the hardware components comprise electrical circuitry subject to the performance assessment.

Example Ex20. The method according to one or more of Ex1 to Ex19, wherein activating comprises activating a microphone and audio processing circuitry of the first hearing device and generating an acoustic test stimulus by an acoustic transducer of the second hearing device, and assessing comprises assessing performance of one or both of the microphone and the audio processing circuitry in response to the acoustic test stimulus.

Example Ex21. The method according to Ex20, wherein the acoustic test stimulus comprises a multi-tone signal or a continuous sweep tone.

Example Ex22. The method according to Ex20, wherein the acoustic test stimulus comprises a continuous sweep tone that sweeps a frequency range of about 100 Hz to about 10 kHz.

Example Ex23. The method according to one or more of Ex1 to Ex22, wherein one or more of the hardware components comprise one or more sensors.

Example Ex24. The method according to Ex23, wherein the one or more sensors comprise one or more of an electrode-based sensor, an optical physiologic sensor, a temperature sensor, a motion sensor, and a biochemical sensor.

Example Ex25. The method according to one or more of Ex1 to Ex24, wherein activating comprises selectively activating a first sensor of the first hearing device and a second sensor of the second hearing device, and assessing comprises assessing performance of one of both of the first hearing device using an output or a response of the second sensor, and the second hearing device using an output or a response of the first sensor.

Example Ex26. The method according to one or more of Ex1 to Ex25, wherein the first hearing device comprises a first sensor and the second hearing device comprises a second sensor. Selectively activating comprises activating the first sensor and one or both of the second sensor and a second electronic component of the second hearing device, and activating the second sensor and one or both of the first sensor and a first electronic component of the second hearing device. Assessing comprises assessing performance of the first hearing device using an output or a response of one of both of the second component and the second electronic component, and assessing performance of the second hearing device using an output or a response of one of both of the first component and the first electronic component.

Example Ex27. The method according to one or more of Ex1 to Ex26, wherein the first hearing device comprises a first sensor and the second hearing device comprises a second sensor. The first sensor comprises a plurality of first hardware components C1 through CN1, where N1 is an integer greater than 2, and the second sensor comprises a plurality of second hardware components C2 through CN2, where N2 is an integer greater than 2. Activating comprises selectively activating different combinations of C1, CN1, C2, CN2, and assessing comprises assessing performance of the first and second sensors by determining which, if any, of C1, CN1, C2, CN2 is performing sub-optimally in response to selective activation of different combinations of C1, CN1, C2, CN2.

Example Ex28. The method according to one or more of Ex1 to Ex27, wherein the first hearing device comprises a first sensor and the second hearing device comprises a second sensor. The first and second sensors comprise first and second optical sensors each comprising hardware components including a light emitter and a light detector. The first optical sensor comprises a first light emitter (E1) and a first light detector (D1), and the second optical sensor comprises a second light emitter (E2) and a second light detector (D2). Activating comprises selectively activating different combinations of E1, D1, E2, D2, and assessing comprises assessing performance of the first and second optical sensors by determining which, if any, of E1, D1, E2, D2 is performing sub-optimally in response to selective activation of different combinations of E1, D1, E2, D2.

Example Ex29. The method according to Ex28, wherein the first and second optical sensors comprise one or more of a PPG sensor, a pulse oximeter, a blood oxygen ($SpO_2$) sensor, a heart rate sensor, and a respiration sensor.

Example Ex30. The method of Ex28 or Ex29, comprising calibrating the first optical sensor using light produced by the second optical sensor, and calibrating the second optical sensor using light produced by the first optical sensor.

Example Ex31. The method according to one or more of Ex1 to Ex30, wherein each of the first and second hearing devices comprises a motion sensor, selectively activating comprises generating, by the second hearing device, an acoustic test stimulus that can excite a first motion sensor of the first hearing device, and assessing comprises assessing performance of the first motion sensor using a response of the first motion sensor to the acoustic test stimulus.

Example Ex32. The method according to Ex31, wherein each of the first and second hearing devices comprises an orientation sensor. Activating within the charger comprises generating, by the second hearing device, an orientation reference point that can be cross checked by the first orientation sensor of the first hearing device, and assessing against a known use case orientation of the charger allows assessing one or both of performance and calibration of the first orientation sensor using a response of the first orientation sensor to the test stimulus.

Example Ex33. The method according to one or more of Ex1 to Ex32, wherein each of the first and second hearing devices comprises a motion sensor and a vibratory transducer. Selectively activating comprises activating a first motion sensor of the first hearing device and a second vibratory transducer of the second hearing device, and assessing comprises assessing performance of the first motion sensor using a vibratory output of the second vibratory transducer.

Example Ex34. The method according to one or more of Ex1 to Ex33, wherein each of the first and second hearing devices comprises at least one temperature sensor. Selectively activating comprises generating heat by the second hearing device and activating a first temperature sensor of the first hearing device, and assessing comprises assessing performance of the first temperature sensor in response to the heat generated by the second hearing device.

Example Ex35. The method according to Ex34, wherein the second hearing device generates heat in response to charging via the charging case while the first hearing device is not subject to charging.

Example Ex36. The method of Ex34 or Ex35, comprising calibrating the at least one temperature sensor after expiration of a predetermined time period after detecting closure of the charging case lid.

Example Ex37. The method according to one or more of Ex1 to Ex36, wherein each of the first and second hearing devices comprises a transceiver coupled to an antenna. Selectively activating comprises activating a first transceiver of the first hearing device and a second transceiver of the second hearing device, and transmitting a test signal from the second transceiver to the first transceiver. Assessing comprises assessing performance of the first transceiver in response to reception or non-reception of the test signal by the first transceiver.

Example Ex38. The method according to one or more of Ex1 to 37, wherein each of the first and second hearing devices comprises a transceiver coupled to an antenna. Selectively activating comprises activating the first and second transceivers. Assessing, by each of the first and second hearing devices, comprises transmitting a test signal using the antenna. The method comprises collecting reflection coefficient (S11) data comprising a reflection coefficient of the antenna, and assessing comprises determining, by each of the first and second hearing devices, if the first and second transceivers are operating sub-optimally using the reflection coefficient data.

Example Ex39. The method according to one or more of Ex1 to Ex38, wherein each of the first and second hearing devices comprises an NFMI transceiver. Selectively activating comprises activating a first NFMI transceiver of the first hearing device and a second NFMI transceiver of the second hearing device, communicating signals between the first and second NFMI transceivers; and assessing performance comprises checking for sufficient NFMI link margin between the first and second NFMI transceivers using the signals communicated therebetween.

Example Ex40. The method according to one or more of Ex1 to Ex39, wherein each of the first and second hearing devices comprises at least one electrode-based sensor, selectively activating comprises generating a test signal by the second hearing device and activating a first electrode-based sensor of the first hearing device, and assessing comprises assessing performance of the first electrode-based sensor using the test signal received by the first electrode-based sensor.

Example Ex41. The method according to Ex40, wherein that at least one electrode-based sensor comprises one or more of an ECG, EMG, EEG, EOG, ERG, EGC, and GSR sensor.

Example Ex42. The method according to one or more of Ex1 to Ex41, wherein one or more of the hardware components comprise a combination of at least one hardware component and a least one sensor.

Example Ex43. The method according to one or more of Ex1 to Ex42, wherein wirelessly coupling comprises electromagnetically, capacitively, inductively or magnetically coupling the first and second hearing devices.

Example Ex44. The method according to one or more of Ex1 to Ex43, wherein wirelessly coupling comprises acoustically coupling the first and second hearing devices.

Example Ex45. The method according to one or more of Ex1 to Ex44, wherein wirelessly coupling comprises optically coupling the first and second hearing devices.

Example Ex46. The method according to one or more of Ex1 to Ex45, wherein the method is implemented concurrently with charging of the first and second hearing devices via the charging case.

Example Ex47. The method according to one or more of Ex1 to Ex46, wherein the method is implemented during a pause in charging of the first and second hearing devices via the charging case.

Example Ex48. The method according to one or more of Ex1 to Ex47, wherein the method is implemented at least once per 24-hour day.

Example Ex49. An ear-wearable electronic device comprising one or more processors configured to implement one or more of method Ex1 to method Ex48.

Example Ex50. The device of Ex49, wherein the device is configured as a personal sound amplification device.

Example Ex51. The device of Ex49, wherein the device is configured as a hearing aid.

Example Ex52. The device of Ex49, wherein the device is configured as a physiologic monitoring device.

Example Ex53. A method comprises initiating, with first and second hearing devices positioned in a charging case, a self-check protocol by at least one of the first and second hearing devices, the self-check protocol comprising wirelessly coupling the first and second hearing devices, activating a first microphone of the first hearing device and generating an acoustic test stimulus by a second acoustic transducer of the second hearing device, and assessing performance of the first microphone in response to the acoustic test stimulus by comparing a response of the first microphone to a pre-established profile representative of nominal microphone performance and detecting sub-optimal performance of the first microphone in response to measuring a specified deviation from the pre-established profile. The method comprises activating a second microphone of the second hearing device and generating an acoustic test stimulus by a first acoustic transducer of the first hearing device, and assessing performance of the second microphone in response to the acoustic test stimulus by comparing a response of the second microphone to the pre-established profile and detecting sub-optimal performance of the second microphone in response to measuring a specified deviation from the pre-established profile. The method also comprises storing results of the performance assessment in a memory, such as a memory of the first and/or second hearing devices.

Example Ex54. The method of Ex53, wherein the acoustic test stimulus comprises a multi-tone signal.

Example Ex55. The method of Ex53, wherein the acoustic test stimulus comprises a continuous sweep tone.

Example Ex56. The method of Ex53, wherein the acoustic test stimulus comprises a continuous sweep tone that sweeps a frequency range of about 100 Hz to about 10 kHz.

Example Ex57. The method of Ex53, wherein the self-check protocol is repeated over time, and the method further comprises tracking changes in performance of the first and second microphones over time, and determining or predicting when performance of the first or second microphone becomes sub-optimal using the tracked performance changes.

Example Ex58. Ear-wearable electronic devices configured to facilitate performance of a self-check protocol within a charging case, the devices comprising a first hearing device and a second hearing device each comprising a microphone, an acoustic transducer, a communication device, and a controller coupled to memory. The controller of at least one of the first and second hearing devices is configured to activate a first microphone of the first hearing device and generate an acoustic test stimulus by a second acoustic transducer of the second hearing device, and assess performance of the first microphone in response to the acoustic test stimulus by comparing a response of the first microphone to a pre-established profile representative of nominal microphone performance and detecting sub-optimal performance of the first microphone in response to measuring a specified deviation from the pre-established profile. The controller is also configured to activate a second microphone of the second hearing device and generate an acoustic test stimulus by a first acoustic transducer of the first hearing device, and assess performance of the second microphone in response to the acoustic test stimulus by comparing a response of the second microphone to the pre-established profile and detecting sub-optimal performance of the second microphone in response to measuring a specified deviation from the pre-established profile. The controller is also configured to store results of the performance assessment in a memory.

Example Ex59. The devices of Ex58, wherein the acoustic test stimulus comprises a multi-tone signal or a continuous sweep tone.

Example Ex60. The devices of Ex58, wherein the self-check protocol is repeated over time, and the controller is configured to track changes in performance of the first and second microphones over time and determine or predict when performance of the first or second microphone becomes sub-optimal using the tracked performance changes.

Figure 1B:
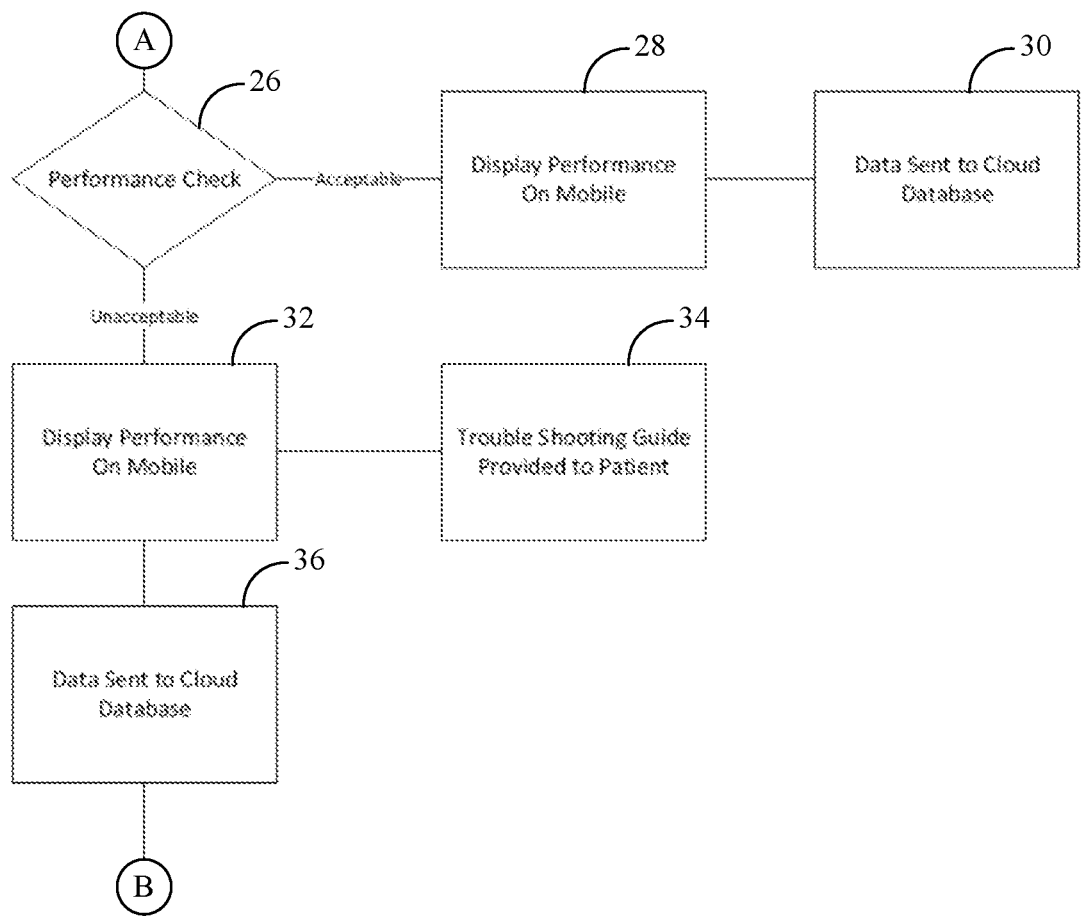
Figure 1C:
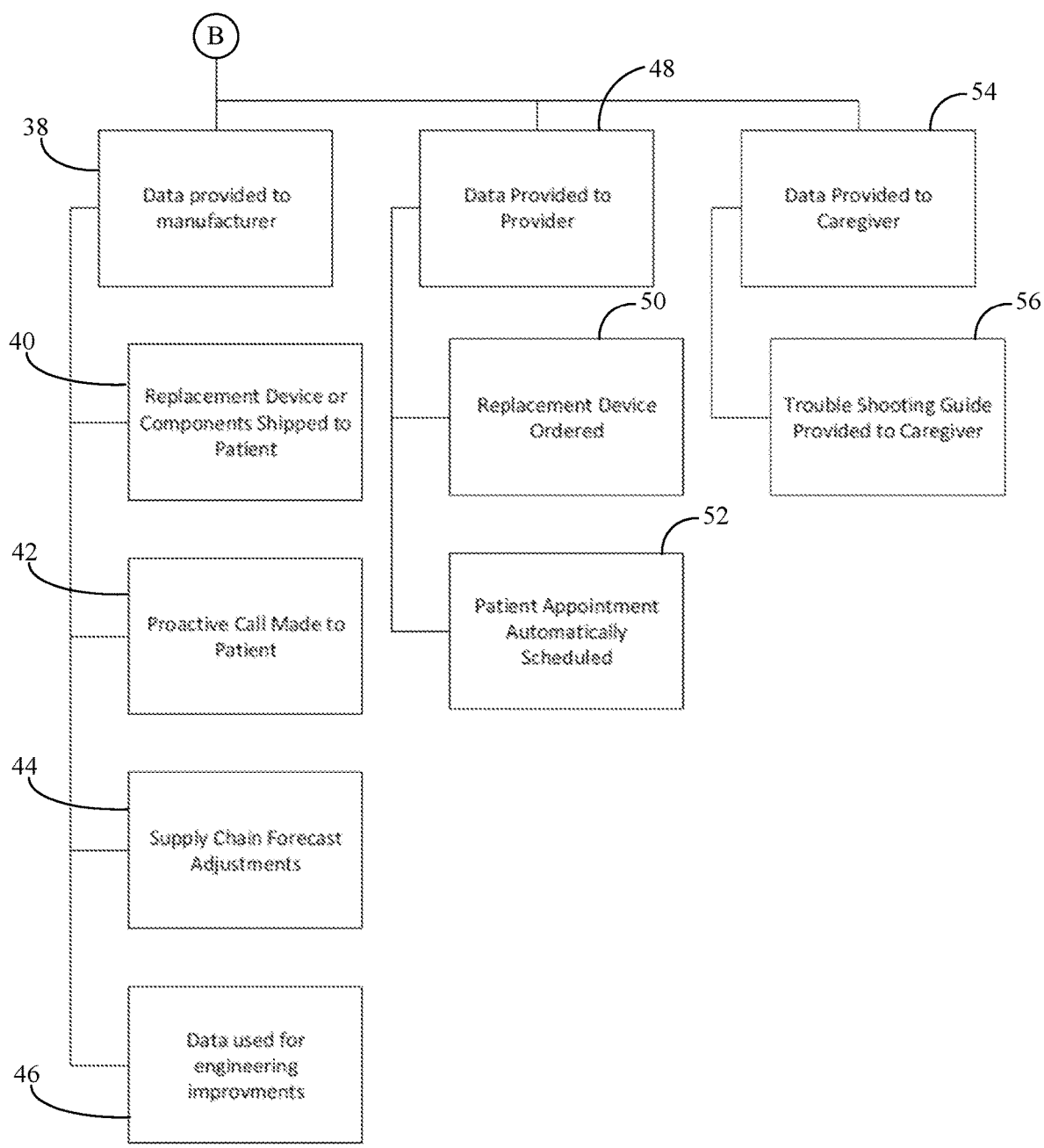

FIGS. 1A-1C illustrate a method which includes a Self-Check protocol in accordance with any of the embodiments disclosed herein. The method shown in FIGS. 1A-1C involves placing 10 a pair of hearing devices in a charging case configured to charge the hearing devices. A lid closure sensor of the charging case is configured to sense 12 whether or not the lid of the charging case is closed. If the sensor determines that the lid is open, the Self-Check protocol is not performed 14. If the sensor determines that the lid is closed, the Self-Check protocol is initiated 16. During execution of the Self-Check protocol, data is stored in a memory of one or both of the hearing devices. Also during execution of the Self-Check protocol, the hearing devices are charged 20 using charge circuitry of the charging case and the hearing devices. It is noted that certain Self-Check protocols may require temporary suspension of charging of one or both hearing devices.

In some implementations, assessing the health of the hearing devices can be implemented using computing resources of the hearing devices operating on the data stored in hearing device memory. In other implementations, assessing the health of the hearing devices can be implemented using an external electronic device, such as a smartphone, tablet, laptop, wireless access point or cloud server (e.g., via the Internet). The Self-Check protocol can include one or more of the protocols disclosed herein (see, e.g., FIGS. 5-20).

After charging the hearing devices, the hearing devices are removed 22 from the charging case. In accordance with any of the disclosed embodiments, the hearing devices are wirelessly connected to an external electronic device, and data acquired by the hearing devices are communicated 24 to the external electronic device. The external electronic device initiates a performance check 26 to determine if each of the hearing devices is performing nominally or sub-optimally. If hearing device performance is determined to be acceptable, performance data is displayed 28 on the external electronic device and the performance data (which may include raw or processed Self-Check protocol data) is communicated 30 to a cloud database. If hearing device performance is determined to be unacceptable, performance data (e.g., sub-optimal performance data) is displayed 32 on the external electronic device and the performance data (which may include raw or processed Self-Check protocol data) is communicated 36 to the cloud database.

As is shown in FIG. 1C, hearing device performance data stored in the cloud database can be accessed by and/or communicated to various users including, for example, the hearing device manufacturer, the hearing device provider (e.g., hearing device professional, audiologist, retailer), and caregivers (e.g., clinicians, family members). In response to analyzing the hearing device performance data, the manufacturer may perform a number of different tasks including replacing 40 a defective or poorly performing hearing device and/or shipping a hearing device component or components to the wearer (e.g., a patient prescribed a hearing aid) of the hearing device. The manufacturer may make a proactive call 42 to the hearing device wearer to alert the wearer of a defective or poorly performing hearing device. The manufacturer may make adjustments 44 in their supply chain forecast in view of the hearing device performance data. The performance data may also be used 46 for engineering/design improvements.

Hearing device performance data can be provided 48 to the hearing device provider, such as a hearing device professional, audiologist, or retailer. In response to the hearing device performance data, the provider can order 50 a replacement hearing device. The hearing device performance data can also be used by the provider to automatically schedule 52 an appointment with the patient, which can allow for personal assessment of hearing device performance by the provider. Hearing device performance data can also be provided 54 to a caregiver of the hearing device wearer. A troubleshooting guide can be provided 56 to the caregiver the of the cloud database. The troubleshooting guide can be used to perform a rudimentary assessment of the hearing device by the caregiver and/or the hearing device wearer.

Figure 2A:
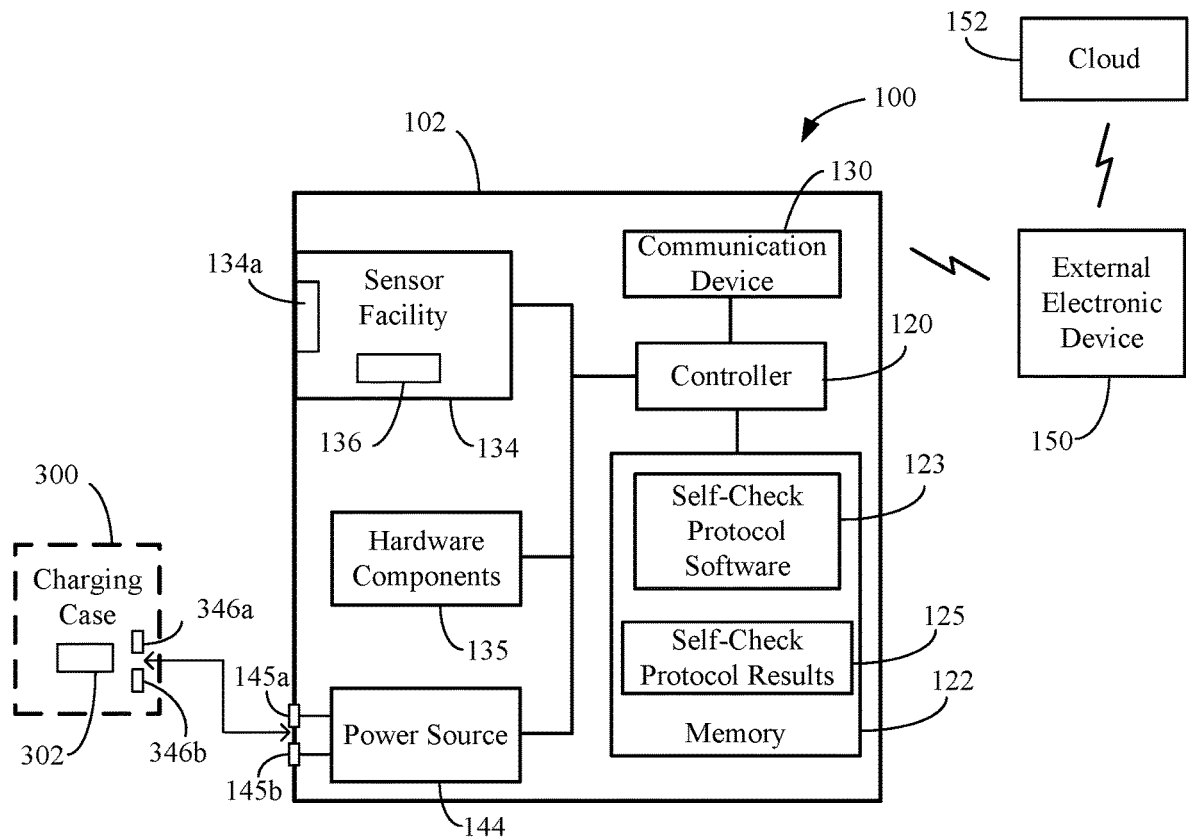
FIG. 2A is a block diagram of an ear-wearable electronic device configured to implement a Self-Check protocol in accordance with any of the embodiments disclosed herein.

FIG. 2A is a block diagram of an ear-wearable electronic device 100 configured to implement a Self-Check protocol in accordance with any of the embodiments disclosed herein. The device 100 is representative of a wide variety of electronic devices configured to be deployed in, on or about an ear of a wearer. In some implementations, the device 100 can be deployed in, on or about one ear of the wearer (e.g., left or right ear). In other implementations, a first device 100 can be deployed in, on or about the wearer's left ear, and a second device 100 can be deployed in, on or about the wearer's right ear. The first and second devices 100 can operate cooperatively (e.g., via an inductive or radio frequency ear-to-ear link) or independently.

The term ear-wearable electronic device (e.g., device 100) refers to a wide variety of electronic devices configured for deployment in, on or about an ear of a wearer. Representative ear-wearable electronic devices of the present disclosure include, but are not limited to, in-the-canal (ITC), completely-in-the-canal (CIC), invisible-in-canal (IIC), in-the-ear (ITE), receiver-in-canal (RIC), behind-the-ear (BTE), and receiver-in-the-ear (RITE) type devices. Representative ear-wearable electronic devices of the present disclosure include, but are not limited to, earbuds, electronic ear plugs, personal sound amplification devices, and other ear-wearable electronic appliances. Ear-wearable electronic devices of the present disclosure include various types of hearing devices, various types of physiologic monitoring and biometric devices, and combined hearing/physiologic monitoring devices. Ear-wearable electronic devices of the present disclosure include restricted medical devices (e.g., devices regulated by the U.S. Food and Drug Administration), such as hearing aids. Ear-wearable electronic devices of the present disclosure include consumer electronic devices, such as consumer earbuds, consumer sound amplifiers, and consumer hearing devices (e.g., consumer hearing aids and over-the-counter (OTC) hearing devices), for example.

The ear-wearable electronic device 100 shown in FIG. 2A includes a housing 102 configured for deployment in, on or about an ear of a wearer. According to any of the embodiments disclosed herein, the housing 102 can be configured for deployment at least partially within the wearer's ear. For example, the housing 102 can be configured for deployment at least partially or entirely within an ear canal of the wearer's ear. The housing 102 can be configured for deployment at least partially within the outer ear, such as from the helix to the ear canal (e.g., the concha cymba, concha cavum) and can extend up to or into the ear canal. In some configurations, the shape of the housing 102 can be customized for the wearer's ear canal (e.g., based on a mold taken from the wearer's ear canal). In other configurations, the housing 102 can be constructed from pliant (e.g., semisoft)

material that, when inserted into the wearer's ear canal, takes on the shape of the ear canal.

The housing 102 is configured to contain or support a number of components 135, referred to herein as "hardware components" for convenience. The hardware components 135 can include one or more electrical, electronic, optical, optoelectronic, optoelectrical, electromagnetic, magnetic, thermal, electromechanical, and mechanical components. FIGS. 2A, 4A-4B, and 5 show a number of representative hardware components 135. In some implementations, the housing 102 is configured to contain or support a sensor facility 134 comprising one or more sensors 134a-134n. The sensor facility 134 can include or be coupled to signal processing circuitry 136 configured to process sensor signals prior to communication of the sensor signals to a controller 120 coupled to a memory 122. The memory 122 is configured to store Self-Check protocol software 123, which includes program instructions executable by the controller 120, which may be implemented as, or comprises, a programmable logic device or processor, for example.

As will be described in greater detail hereinbelow, the controller 120 is configured to execute Self-Check protocol program instructions 123 to assess the operational "health" of two or more devices 100 when placed in a charging case configured to receive the two or more devices 100. Results 125 of the Self-Check protocol assessment can be stored in the memory 122 of one or more of the devices 100, a memory of the charging case, an external electronic device 150 configured to communicatively couple to the devices 100 via a communication device 130 (e.g., a wireless transceiver), and/or the cloud 152 (e.g., a cloud server or cloud storage) via the communication device 130 directly or indirectly via the external electronic device 150. As previously mentioned, the external electronic device 150 can be a smartphone, mobile phone, tablet, laptop, and/or wireless access point.

A power source 144, such as a rechargeable battery (e.g., lithium-ion battery), is configured to provide power to various components of the device 100. The power source 144 of the devices 100 is configured to receive power from a power source 302 (e.g., a rechargeable battery) of the charging case 300 during a charging procedure. When the devices 100 are properly positioned in the charging case 300, charge contacts 145a, 145b of the devices 100 electrically couple to corresponding charge contacts 346a, 346b of the charging case 300. In some implementations, the charge contacts 145a, 145b 346a, 346b are inductive components configured to facilitate wireless charging of the power source 144.

The hardware components 135 include one or more electrical, electronic, optical, optoelectronic, optoelectrical, electromagnetic, magnetic, thermal, electromechanical, and mechanical components. The hardware components 135 comprise one or both of a passive hardware components and an active hardware components. Representative hardware components include, but are not limited to, one or more of a processor, a logic device, a DSP, and audio signal processor, a memory, a power source, a radio, a transceiver, a microphone, an acoustic transducer, a user interface, an antenna, a telecoil, and NFMI device, a PCBA, electrical circuitry, electronic circuitry, and optoelectronic circuitry.

Figure 2B:
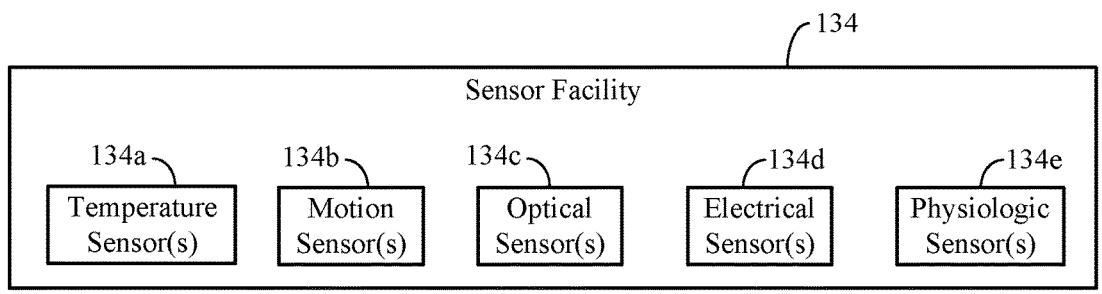
FIG. 2B shows a representative sensor facility of the ear-wearable electronic device shown in FIG. 2A.

In some implementations, the device 100 includes a sensor facility 134 which includes one or more sensors. FIG. 2B shows a representative sensor facility 134 which includes one or more temperature sensors 134a, such as one or more thermistors, thermocouples or RTDs (resistance temperature detector). The sensor facility 134 can include one or more motion sensors 134b, one or more optical (e.g., optoelectrical or optoelectronic) sensors 134c, and one or more electrical sensors 134d (e.g., electrode-based sensors). Signals generated by any one or any combination of the temperature sensors 134a, motion sensors 134b, optical sensors 134c, electrical sensors 134d, and physiologic sensors 134e can be used by the controller 120 when performing a Self-Check protocol in accordance with any of the disclosed embodiments to assess the health of the devices 100.

The one or more motion sensors 134b can include one or more of accelerometers, gyros, and magnetometers. For example, the motion sensor 134b can be implemented to include a multi-axis (e.g., 9-axis) sensor, such as an IMU (inertial measurement unit). A suitable IMU is disclosed in commonly owned U.S. Pat. No. 9,848,273, which is incorporated herein by reference.

The one or more optical sensors 134c can include a photoplethysmography (PPG) sensor, such as a pulse oximeter. The one or more electrical sensors 134d can include one or more sensors configured to contact the skin of the wearer's ear and sense a change in an electrical property of the skin. For example, the one or more electrical sensors 134d can be configured to sense one or any combination of impedance, conductance, resistance, and electrodermal activity (e.g., galvanic skin response).

The sensor facility 134 of the device 100 can include one or more physiologic or biometric sensors 134e. The physiologic/biometric sensors 134e can include one or more of an EKG or ECG sensor, a pH sensor, an $SpO_2$ sensor, a blood pressure sensor, a respiration sensor, a glucose sensor, an EEG sensor, an EMG sensor, an EOG sensor, an ERG sensor, and an electrodermal activity (e.g., GSR) sensor. Representative examples of such sensors are disclosed in US Pat. Pub. Nos. 2018/0014784 (Heeger et al.), 2013/0216434 (Ow-Wing), and 2010/0253505 (Chou), and in U.S. Pat. No. 9,445,768 (Alexander et al.) and U.S. Pat. No. 9,107,586 (Bao), each of which is incorporated herein by reference in its entirety. It is noted that the device 100 can be implemented as a biometric sensing device which may include or exclude a hearing assistance or audio processing/output facility.

The communication device 130 can include a radiofrequency (RF) transceiver and antenna and/or a near field magnetic induction (NFMI) transceiver and antenna. For example, the communication device 130 can incorporate an antenna arrangement coupled to a high-frequency radio, such as a 2.4 GHz radio. The radio can conform to an IEEE 802.11 (e.g., WiFi®) or Bluetooth® (e.g., BLE, Bluetooth® 4.2, 5.0, 5.1, 5.2 or later) specification, for example. Sensor signals generated by the sensor facility 134 can be communicated to the external electronic device 150 and to the cloud 152 via the communication device 130.

Figure 3:
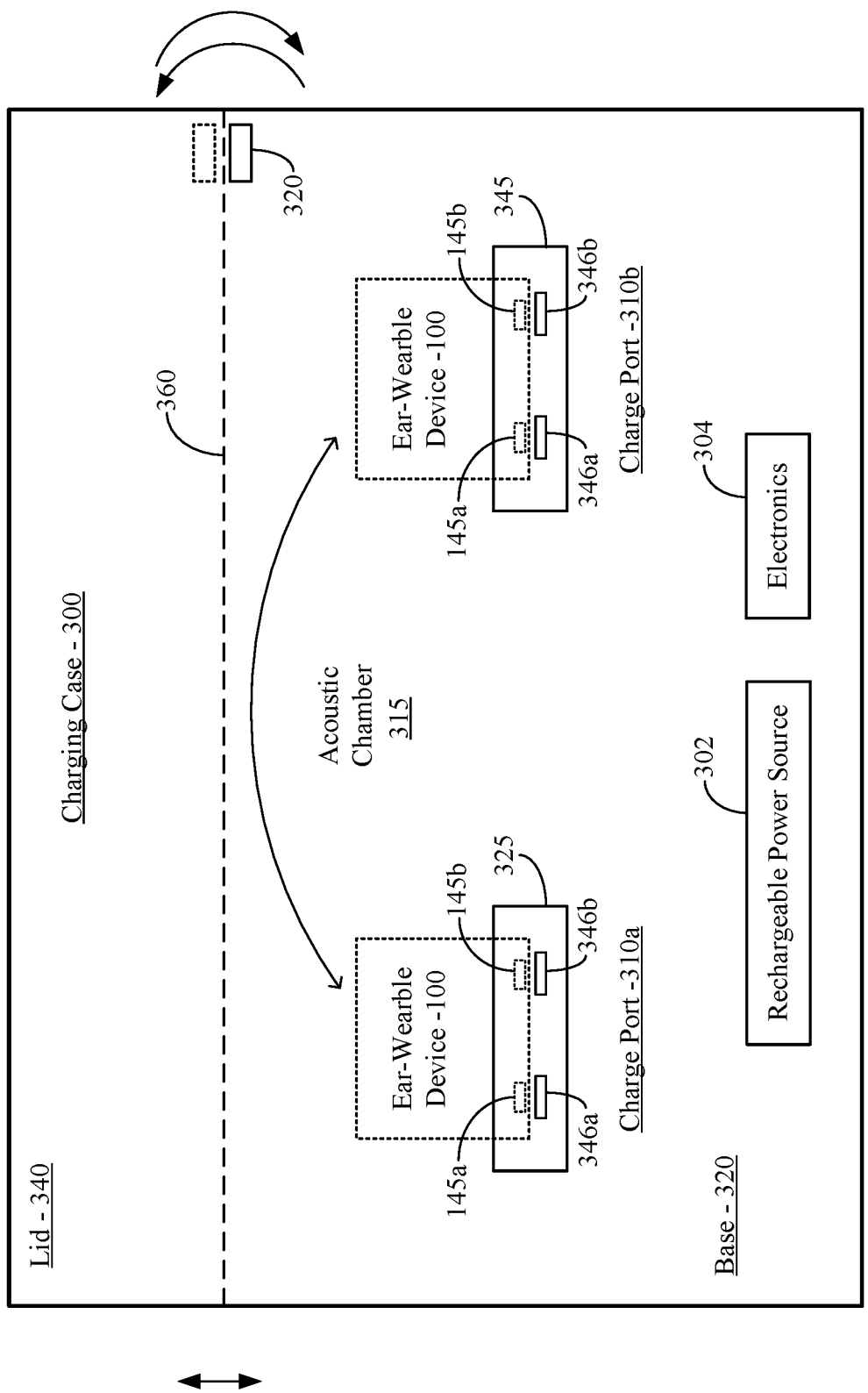
FIG. 3 illustrates a charging case in accordance with any of the embodiments disclosed herein.

FIG. 3 illustrates a charging case 300 in accordance with any of the embodiments disclosed herein. The charging case 300 includes a base 320 and a lid 340 movably connected to the base 320. The charging case 300 illustrated in FIG. 3 is in a closed position such that the lid 340 is proximate or covering the base 320, and vice versa. In the closed position, an acoustic chamber 315 is defined in the space between the base 320 and the lid 340. The base and lid 320, 340 can include sound insulation to reduce external sound from reaching the acoustic chamber 315. A seal can be disposed between the base 320 and the lid 340 to enhance sound insulation of the charging case 300.

The base 320 and the lid 340 may be movably coupled in any suitable way. For example, the charging case 300 can include one or more hinges 360 operably coupled between the base and lid 320, 340. As such, the base 320 and the lid 340 may rotate about the hinge 360 and move relative to one another. In some implementations, the base and lid 320, 340 define a two-part separable structure, in which the lid 340 is separable from the base 320 in response to manual force. The base 320 and/or the lid 340 includes a sensor 320 configured to sense opening and closing of the charging case 300. The sensor 320 can be an electrical, capacitive, electromechanical, optical or magnetic sensor or switch.

When the charging case 300 is in an open position, hearing devices 100 may be positioned within charge ports 310a, 310b provided in the base 320 (e.g., within first and second cavities 325, 345, respectively). The hearing devices 100 may include any type of hearing device, such as those listed above. Further, the first and second cavities 325, 345 may be any suitable size and/or shape to receive any type of hearing device. In some embodiments, the charging case 300 may include an adapter to modify the cavities 325, 345 to receive different sized hearing devices 100. By positioning the hearing devices within the cavities 325, 345, the hearing devices may be protected from being damaged due to, e.g., bending, twisting, or other force-induced failure. The charging case 300 may be configured to be portable and sized for transport on the wearer's person (e.g., clothing, purse, backpack, fanny pack). The charging case 300 can alternatively be representative of a console or desk-top (e.g., bedside) charger.

The charging contacts 346a, 346b of the charging case 300 may include a biasing element (e.g., a spring) that aids in retaining the hearing devices 100 within the cavity 325, 345 (e.g., by applying a force to the hearing devices 100 against the cavities 325, 345). Further, the shape of the cavities 325, 345 may automatically position the hearing device correctly within the cavities 325, 345 such that the charging contacts 145a, 145b of the hearing devices 100 properly align with the charging contacts 346a, 346b of the charging case 300. As a result, if the charging case 300 is moved to the closed position, the hearing devices 100 will be correctly positioned to charge. Also, no additional latches may be needed to retain the hearing devices 100 within the cavities 325, 345.

For example, in some embodiments, the biasing elements of the charging contacts 346a, 346b may include magnets to align the charging contacts 346a, 346b to the hearing devices 100. For example, the magnets of the biasing elements may create a tactile sensation such that the hearing devices 100 "snap" into place and make contact with the charging contacts 346a, 346b (e.g., without additional manipulation of the device by the user). Specifically, the corresponding magnets of the hearing devices 100 may be added in a planar fashion (e.g., instead of linear) as it relates to the axis of the magnet. Therefore, the sensation resulting from connecting the hearing devices 100 within the cavities 325, 345 (e.g., connecting the charging contacts 346a, 346b to the charging contacts 145a, 145b of the hearing devices 100) may provide a feeling of the hearing devices 100 "jumping" into place.

When the hearing devices 100 are received by the corresponding cavity 325, 345, charging contacts 145a, 145b of the hearing devices 100 electrically or inductively couple to corresponding charging contacts 346a, 346b of the charging case 300. In some implementations, the charging contacts 145a, 145b, 346a, 346b are implemented as electrical contacts, such that charging of the hearing devices 100 is performed using a wired connection (e.g., wired charging). In other implementations, the charging contacts 145a, 145b, 346a, 346b are implemented as inductive (or capacitive) contacts or components, such that charging of the hearing devices 100 is performed using a wireless connection (e.g., wireless charging, such as in conformance with a Qi wireless charging protocol)).

A rechargeable power source 302 (e.g., a lithium-ion battery) of the charging case 300, which includes or is coupled to charging circuitry (e.g., power management IC or PMIC), is configured to initiate a programmed charging protocol after the hearing devices 100 are received by the corresponding cavity 325, 345. In some implementations, charging of the hearing device 100 is initiated after the base and lid 320, 340 are moved to their closed positions, thereby reconstituting the acoustic chamber 315.

As previously discussed, the charging case 300 includes a rechargeable power source 302 and also includes electronics 304 (e.g., a PMIC) for charging the hearing devices 100 (which also contain a rechargeable power source 144 and a PMIC) when contained within the charging case 300. For example, the rechargeable power source 302 may be disposed in one of the base and lid 320, 340 and the electronics 304 may be disposed in the other of the base and lid 320, 340. It is noted that while the rechargeable power source 302 and electronics 304 can be located within separate body portions, in some embodiments, the rechargeable power source 302 and the electronics 304 may be located in the same body portion (e.g., the base 320 or the lid 340).

The electronics 304 may be implemented, at least in part, in hardware, software, firmware, or any combination thereof. For example, various aspects of the disclosed Self-Check protocol techniques may be implemented in part with the assistance of the electronics 304. The electronics 304 can include one or more processors, including one or more microprocessors, microcontrollers, DSPs, ASICs, FPGAs, or any other equivalent integrated or discrete logic circuitry, as well as any combinations of such components, or other devices. The electronics 304 can include memory or other computer-readable medium such as RAM, ROM, NVRAM, EEPROM, FLASH memory, magnetic data storage media, optical data storage media, or the like. The electronics 304 can also include one or more microphones, one or more speakers, and audio signal processing circuitry coupled to the microphones and speakers. Instructions and/or logic for cooperating with the hearing devices 100 in the implementation of a Self-Check protocol may be executed by one or more processors of the charging case 300 to support one or more aspects of the functionality described in this disclosure.

Figure 4:
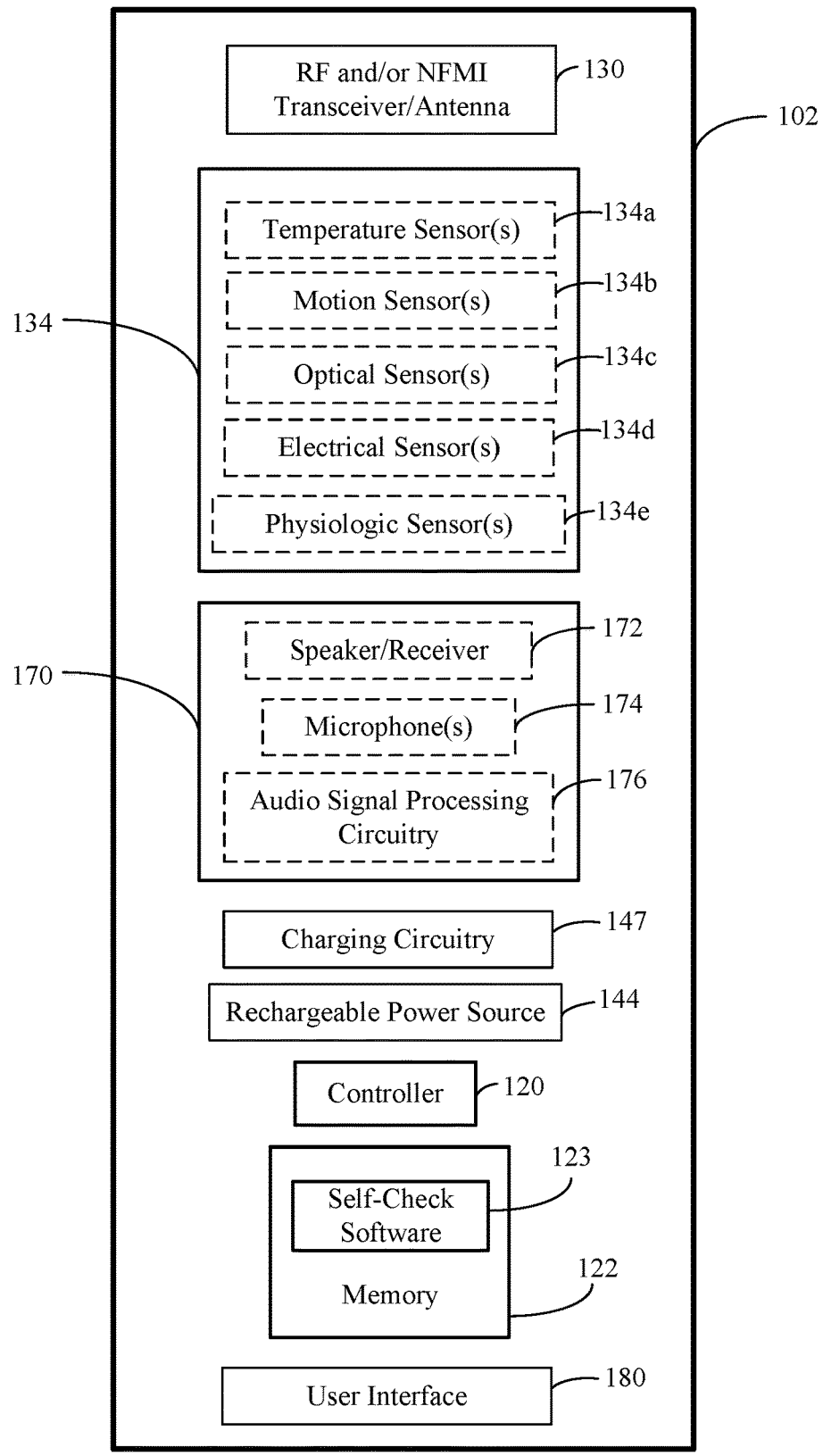
FIG. 4 is a block diagram of an ear-worn electronic device configured to implement a Self-Check protocol in of accordance with any of the embodiments disclosed herein.

FIG. 4 is a block diagram of an ear-worn electronic device 100 configured to implement a Self-Check protocol in of accordance with any of the embodiments disclosed herein. As was previously discussed, the device 100 is representative of a wide variety of electronic devices configured to be deployed in, on or about an ear of a wearer. The device 100 shown in FIG. 4 includes several core components shown in FIG. 2A, including a controller 120 coupled to memory 122 configured to store Self-Check protocol software 123, a sensor facility 134, and a power source 144. In implementations that include a rechargeable power source 144, the device 100 includes charging circuitry 147 coupled to the rechargeable power source 144. The charging circuitry 147 is configured to cooperate with an charging circuitry of the charging case 300 to facilitate charging of the rechargeable power source 144. As was previously discussed, the sensor facility 134 can include one or more temperature sensors 134a, one or more motion sensors 134b, one or more optical sensors 134c, one or more electrical sensors 134d, and/or one or more physiologic sensors 134e.

In some embodiments, the device 100 incorporates an audio processing facility 170. The audio processing facility 170 includes audio signal processing circuitry 176 coupled to a speaker or receiver 172. The audio processing facility 170 may also include one or more microphones 174 coupled to the audio signal processing circuitry 176. In other embodiments, the device 100 is devoid of the audio processing facility 170. The device 100 can also incorporate a communication facility 130 configured to effect communications with an external electronic device, system and/or the cloud. The communication facility 130 can include one or both of an RF transceiver/antenna and/or an NFMI transceiver/antenna.

According to embodiments that incorporate the audio processing facility 170, the device 100 can be implemented as a hearing assistance device that can aid a person with impaired hearing. For example, the device 100 can be implemented as a monaural hearing aid or a pair of devices 100 can be implemented as a binaural hearing aid system. The monaural device 100 or a pair of devices 100 can be configured to effect bi-directional communication (e.g., wireless communication) of data with an external source, such as a remote server via the Internet or other communication infrastructure. The device or devices 100 can be configured to receive streaming audio (e.g., digital audio data or files) from an electronic or digital source. Representative electronic/digital sources (e.g., accessory devices) include an assistive listening system, a streaming device (e.g., a TV streamer or audio streamer), a radio, a smartphone, a laptop, a cell phone/entertainment device (CPED) or other electronic device that serves as a source of digital audio data, control and/or settings data or commands, and/or other types of data files.

The device 100 can also include a user interface 180, which can include manually-actuatable buttons and/or switches (e.g., mechanical, capacitive, and/or optical switches). The user interface 180 may alternatively, or additionally, include a voice recognition interface configured to facilitate wearer control of the device 100 via voice commands. The voice recognition interface is preferably configured to discriminate between vocal sounds produced from the wearer of the device 100 (e.g., "own voice" recognition via an acoustic template developed for the wearer) and vocal sounds produced from other persons in the vicinity of the device 100. The user interface 180 may alternatively, or additionally, include a gesture detection interface configured to facilitate wearer control of the device 100 via gestures (e.g., non-contacting hand and/or finger gestures made in proximity to the device 100). Examples of gesture detection user interfaces and voice recognition user interfaces suitable for incorporation in device 100 are disclosed in U.S. patent application Ser. No. 62/875,139 filed Jul. 17, 2019 and entitled "Ear-Worn Electronic Device Incorporating Gesture Control System Using Frequency-Hopping Spread Spectrum Transmission" and U.S. patent application Ser. No. 62/939,031 filed Nov. 22, 2019 and entitled "Ear-Worn Electronic Device Incorporating Gesture Control System Using Frequency-Hopping Spread Spectrum Transmission," U.S. Pat. Nos. 8,165,329, 9,900,712, and 10,341,784, and U.S. Patent Publication Nos. 2010/0067722, 2011/0238419, and 2011/0261983, each of which is incorporated herein by reference in its entirety.

The controller 120 (and the controller 120 shown in other figures) can include one or more processors or other logic devices. For example, the controller 120 can be representative of any combination of one or more logic devices (e.g., multi-core processor, digital signal processor (DSP), microprocessor, programmable controller, general-purpose processor, special-purpose processor, hardware controller, software controller, a combined hardware and software device) and/or other digital logic circuitry (e.g., ASICs, FPGAs), and software/firmware configured to implement the functionality disclosed herein. The controller 120 can incorporate or be coupled to various analog components (e.g., analog front-end), ADC and DAC components, and Filters (e.g., FIR filter, Kalman filter). The memory 122 can include one or more types of memory, including ROM, RAM, SDRAM, NVRAM, EEPROM, and FLASH, for example. The controller 120 can be coupled to, or incorporate, the memory 122.

Figure 5:
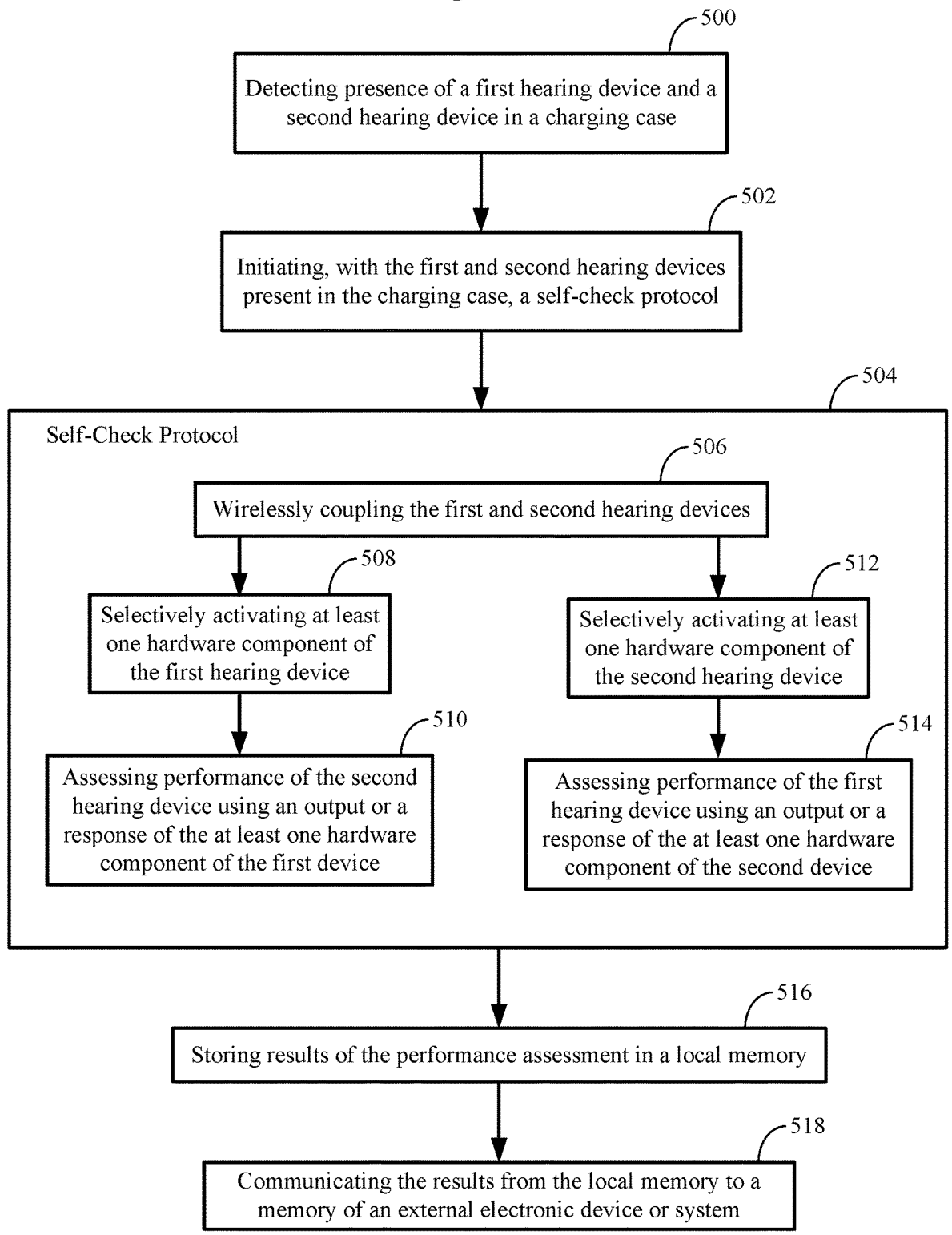
FIG. 5 illustrates a Self-Check protocol in accordance with any of the embodiments disclosed herein.

FIG. 5 illustrates a Self-Check protocol in accordance with any of the embodiments disclosed herein. The method shown in FIG. 5 involves detecting 500 presence of a first hearing device and a second hearing device in a charging case (e.g., in response to a lid sensor close signal). The method involves initiating 502, with the first and second hearing devices present in the charging case, a Self-Check protocol 504. The Self-Check protocol 504 involves wirelessly coupling 506 the first and second hearing devices, and selectively activating 508 at least one hardware component of the first hearing device. The Self-Check protocol 504 involves assessing 510 performance of the second hearing device using an output or a response of the at least one hardware component of the first device. In this and other embodiments, wirelessly coupling the first and second hearing devices comprises one or more of electromagnetically, capacitively, inductively, magnetically, acoustically, and optically coupling the first and second hearing devices.

The Self-Check protocol 504 also involves selectively activating 512 at least one hardware component of the second hearing device. The Self-Check protocol 504 further involves assessing 514 performance of the first hearing device using an output or a response of the at least one hardware component of the second device. The method shown in FIG. 5 involves storing 516 results of the performance assessment in the local memory (e.g., memory of the hearing devices 100 and, additionally or optionally, in memory of the charging case 300). The method may also involve communicating 518 the results stored in local memory to an external electronic device or system (e.g., a smartphone, table, wireless access point, the cloud). The hardware component or components subject to testing can be the same or different components, and can be any hearing device component disclosed herein. The hardware component or components can be, or include, electrical circuitry (e.g., a rigid or flexible PCB) which can be subject to a performance assessment via the Self-Check protocol 504.

Figure 6:
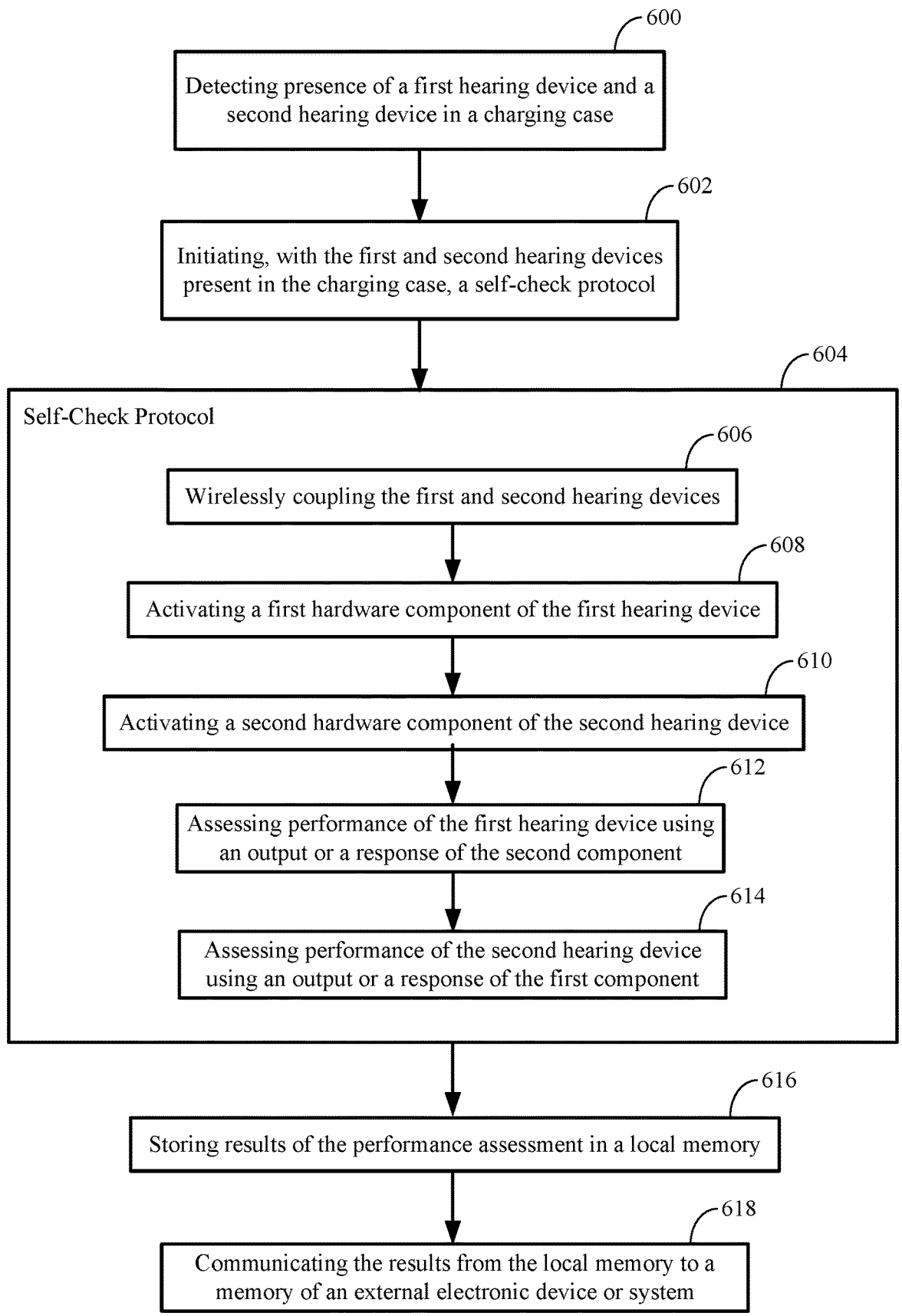
FIG. 6 illustrates a Self-Check protocol in accordance with any of the embodiments disclosed herein.

FIG. 6 illustrates a Self-Check protocol in accordance with any of the embodiments disclosed herein. The method shown in FIG. 6 involves detecting 600 presence of a first hearing device and a second hearing device in a charging case. The method involves initiating 602, with the first and second hearing devices present in the charging case, a Self-Check protocol 604. The Self-Check protocol 604 involves wirelessly coupling 606 the first and second hearing devices, and activating 608 a first hardware component of the first hearing device and activating 610 a second hardware component of the second hearing device. The Self-Check protocol 604 also involves assessing 612 performance of the first hearing device using an output or a response of the second component, and assessing 614 performance of the second hearing device using an output or a response of the first component. The method shown in FIG. 6 involves storing 616 results of the performance assessment in local memory. The method may also involve communicating 618 the results stored in local memory to an external electronic device or system (e.g., a smartphone, table, wireless access point, the cloud). The hardware component or components subject to testing can be the same or different components, and can be any hearing device component disclosed herein. The hardware component or components can be, or include, electrical circuitry (e.g., a rigid or flexible PCB) which can be subject to a performance assessment via the Self-Check protocol 604.

Figure 7:
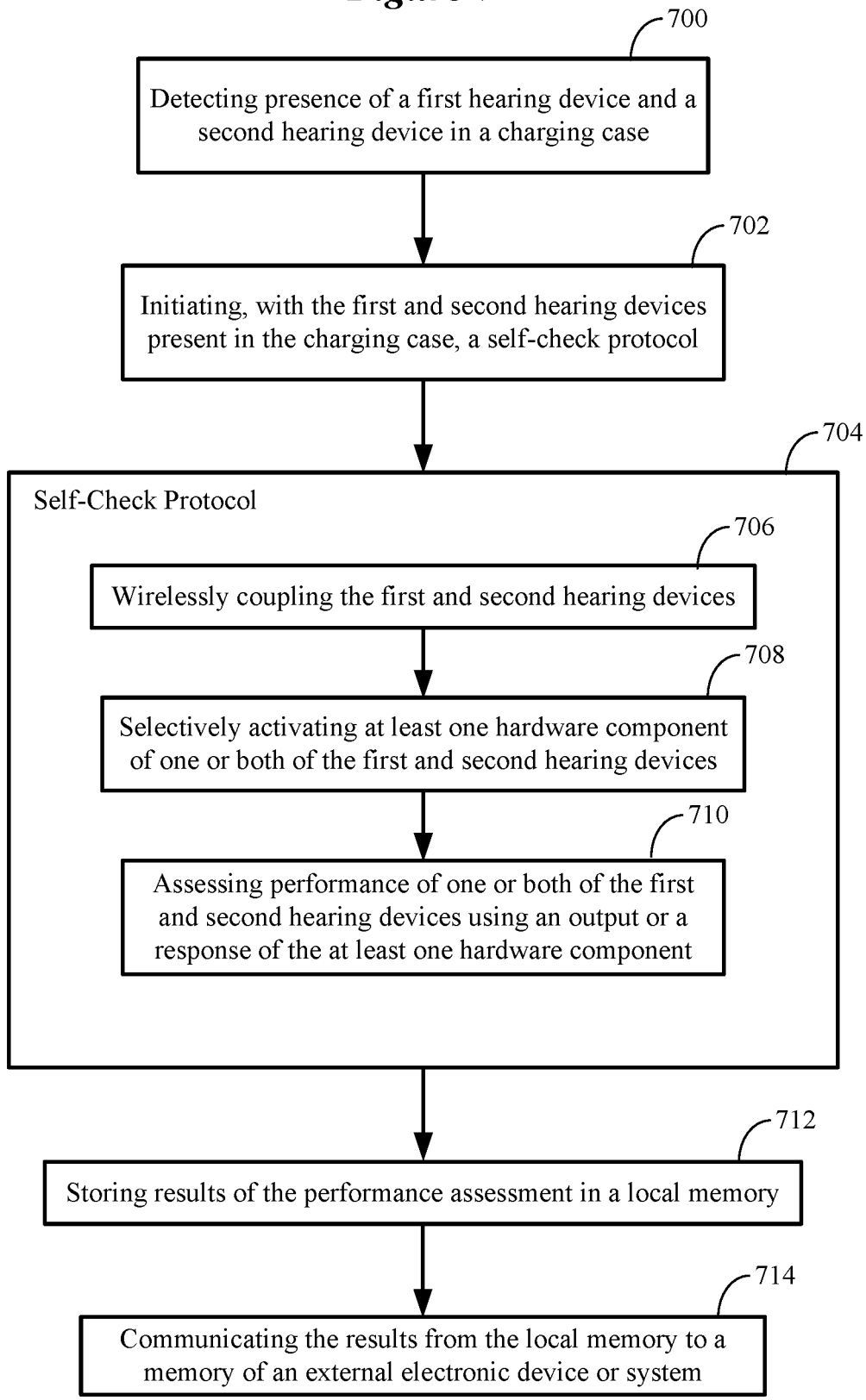
FIG. 7 illustrates a Self-Check protocol in accordance with any of the embodiments disclosed herein.

FIG. 7 illustrates a Self-Check protocol in accordance with any of the embodiments disclosed herein. The method shown in FIG. 7 involves detecting 700 presence of a first hearing device and a second hearing device in a charging case. The method involves initiating 702, with the first and second hearing devices present in the charging case, a Self-Check protocol 704. The Self-Check protocol 704 involves wirelessly coupling 706 the first and second hearing devices, and selectively activating 708 at least one hardware component of one or both of the first and second hearing devices. The Self-Check protocol 704 also involves assessing 710 performance of one or both of the first and second hearing devices using an output or a response of the at least one hardware component. The method shown in FIG. 7 also involves storing 712 results of the performance assessment in the local memory. The method may also involve communicating 714 the results stored in local memory to an external electronic device or system (e.g., a smartphone, table, wireless access point, the cloud). The hardware component or components subject to testing can be the same or different components, and can be any hearing device component disclosed herein. The hardware component or components can be, or include, electrical circuitry (e.g., a rigid or flexible PCB) which can be subject to a performance assessment via the Self-Check protocol 704.

Figure 8:
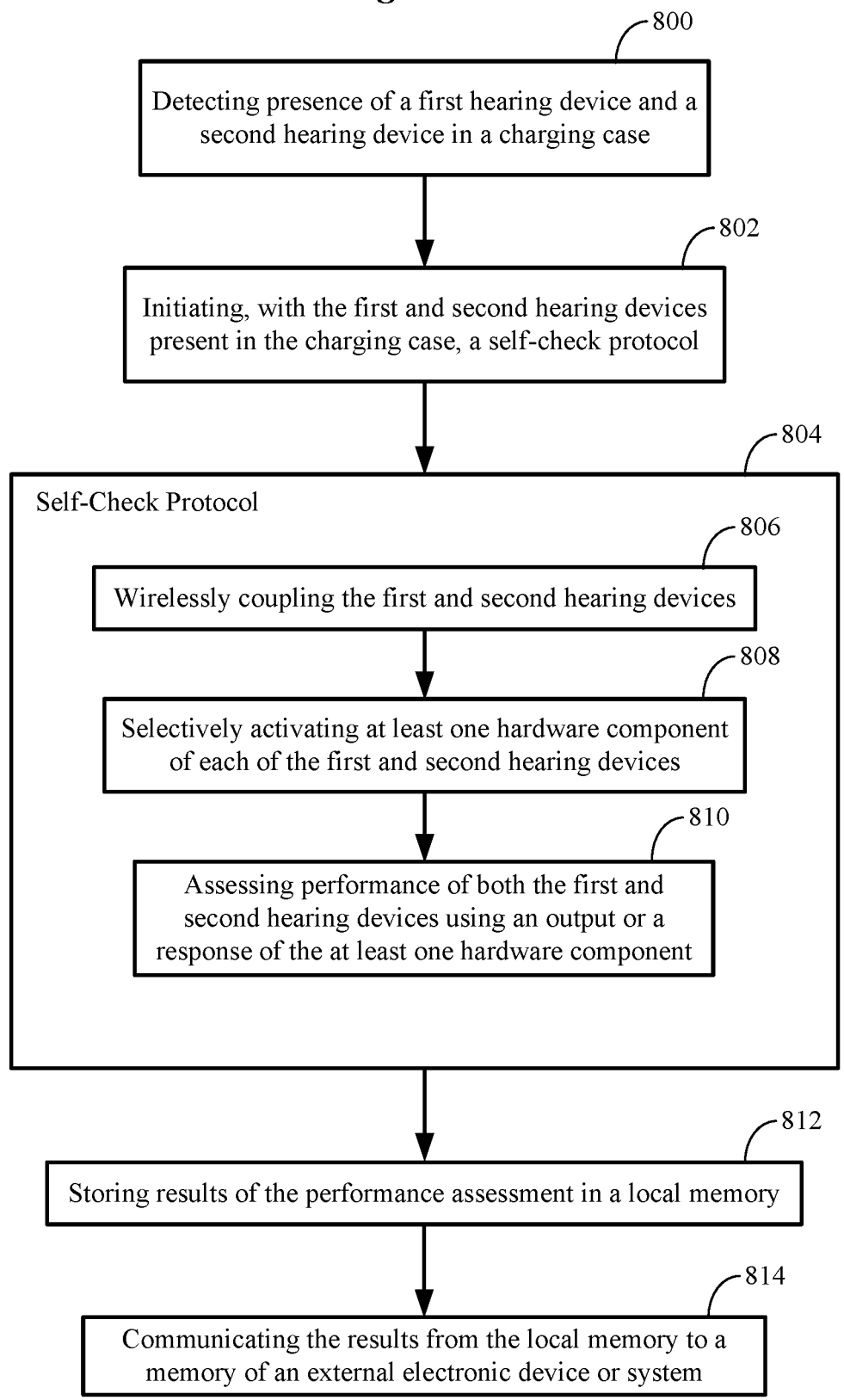
FIG. 8 illustrates a Self-Check protocol in accordance with any of the embodiments disclosed herein.

FIG. 8 illustrates a Self-Check protocol in accordance with any of the embodiments disclosed herein. The method shown in FIG. 8 involves detecting 800 presence of a first hearing device and a second hearing device in a charging case. The method involves initiating 802, with the first and second hearing devices present in the charging case, a Self-Check protocol 804. The Self-Check protocol 804 involves wirelessly coupling 806 the first and second hearing devices, and selectively 808 activating at least one hardware component of each of the first and second hearing devices. The Self-Check protocol 804 also involves assessing 810 performance of one or both of the second hearing devices using an output or a response of the at least one hardware component of each of the first and second hearing devices. The method shown in FIG. 8 also involves storing 812 results of the performance assessment in local memory. The method may also involve communicating 814 the results stored in local memory to an external electronic device or system (e.g., a smartphone, table, wireless access point, the cloud). The hardware component or components subject to testing can be the same or different components, and can be any hearing device component disclosed herein. The hardware component or components can be, or include, electrical circuitry (e.g., a rigid or flexible PCB) which can be subject to a performance assessment via the Self-Check protocol 804.

Figure 9:
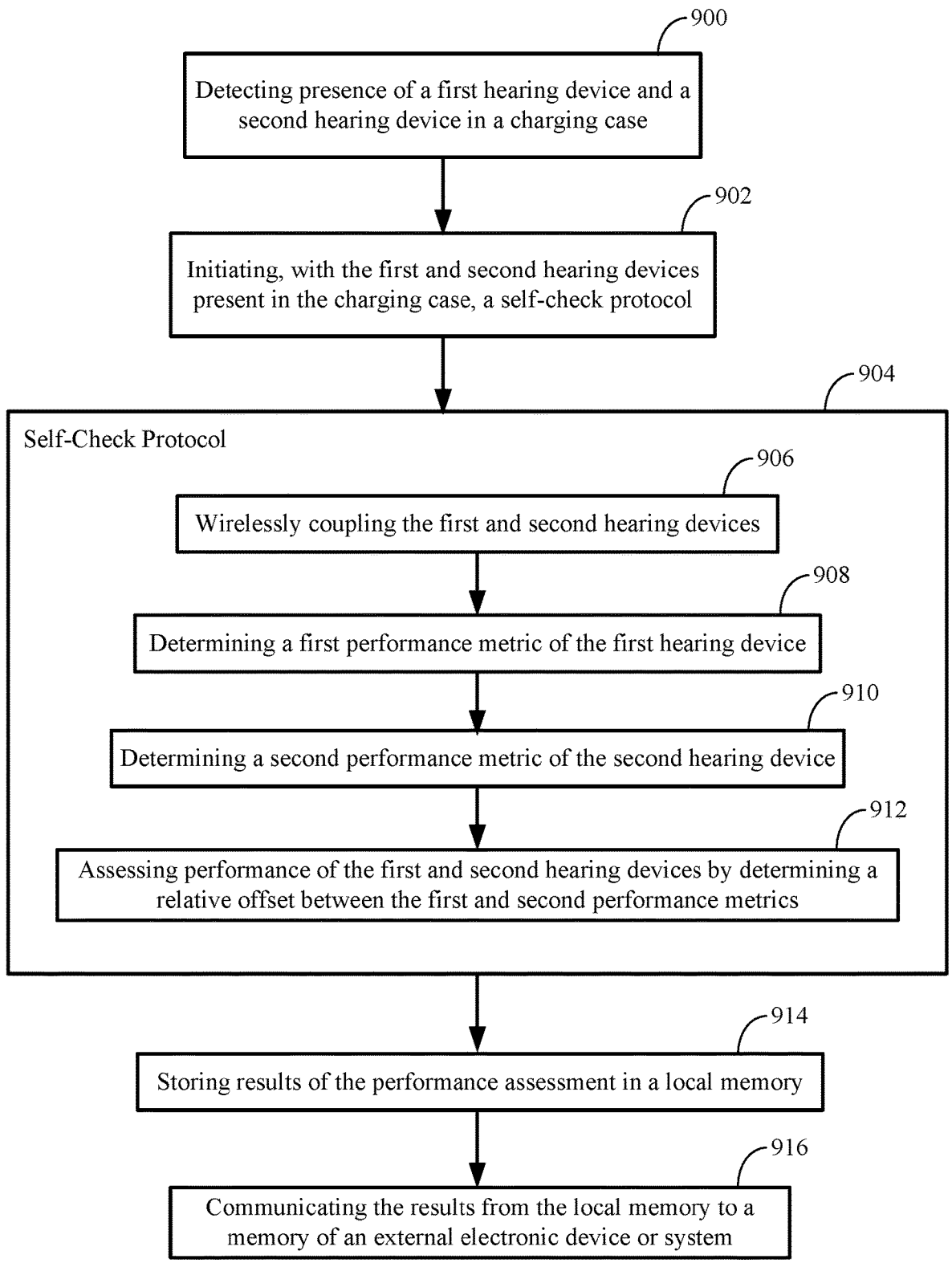
FIG. 9 illustrates a Self-Check protocol in accordance with any of the embodiments disclosed herein.

FIG. 9 illustrates a Self-Check protocol in accordance with any of the embodiments disclosed herein. The method shown in FIG. 9 involves detecting 900 presence of a first hearing device and a second hearing device in a charging case. The method involves initiating 902, with the first and second hearing devices present in the charging case, a Self-Check protocol 904. The Self-Check protocol 904 involves wirelessly coupling 906 the first and second hearing devices, and determining 908 a first performance metric of the first hearing device. The Self-Check protocol 904 also involves determining 910 a second performance metric of the second hearing device. The Self-Check protocol 904 further involves assessing 912 performance of the first and second hearing devices by determining a relative offset between the first and second performance metrics (e.g., which can be compared to a threshold to determine acceptable or unacceptable performance). The method shown in FIG. 9 also involves storing 914 results of the performance assessment in local memory. The method may also involve communicating 916 the results stored in local memory to an external electronic device or system (e.g., a smartphone, table, wireless access point, the cloud). The hardware component or components subject to testing can be the same or different components, and can be any hearing device component disclosed herein. The hardware component or components can be, or include, electrical circuitry (e.g., a rigid or flexible PCB) which can be subject to a performance assessment via the Self-Check protocol 904.

Figure 10:
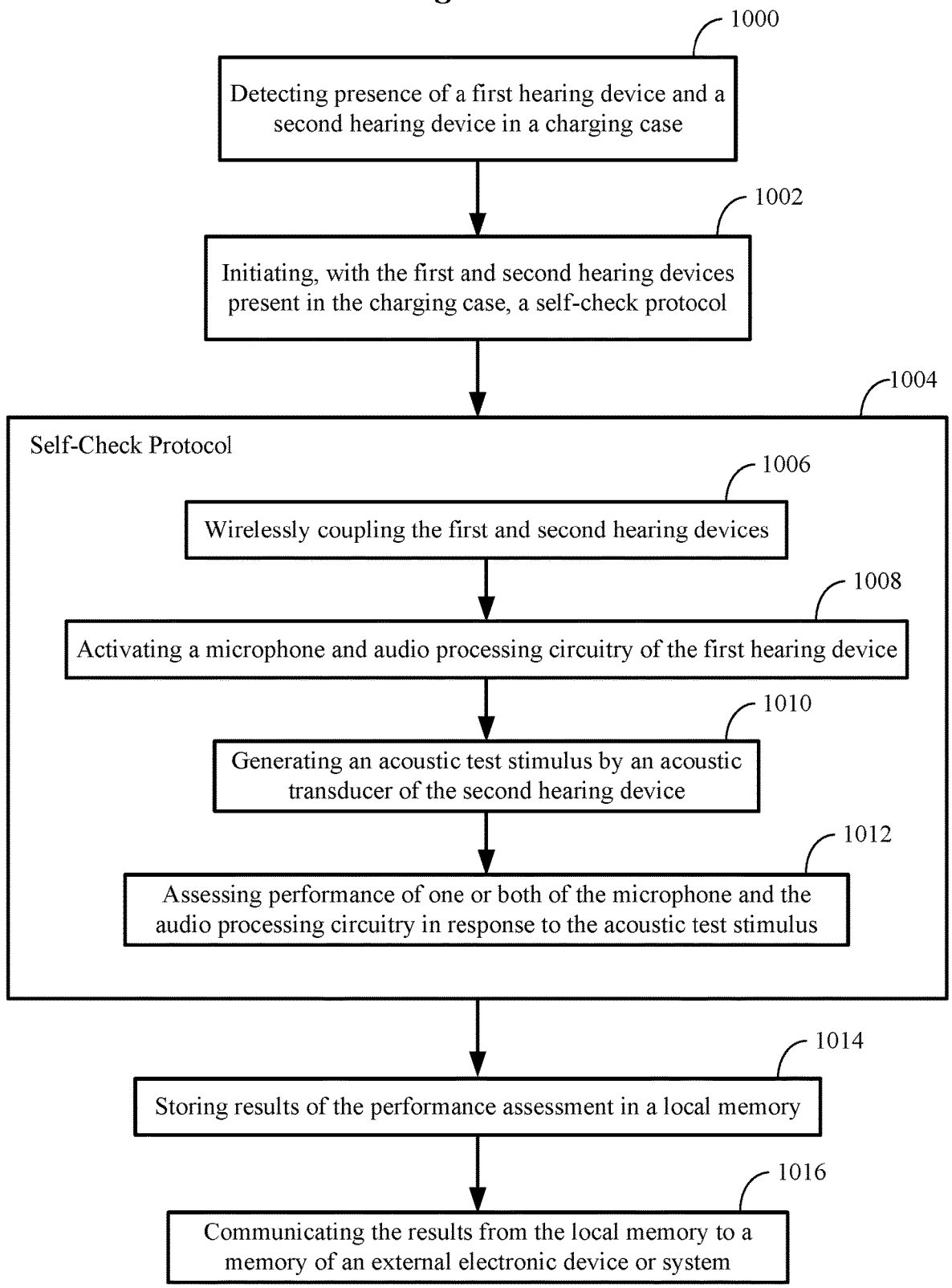
FIG. 10 illustrates a Self-Check protocol in accordance with any of the embodiments disclosed herein.

FIG. 10 illustrates a Self-Check protocol in accordance with any of the embodiments disclosed herein. The method shown in FIG. 10 involves detecting 1000 presence of a first hearing device and a second hearing device in a charging case. The method involves initiating 1002, with the first and second hearing devices present in the charging case, a Self-Check protocol 1004. The Self-Check protocol 1004 involves wirelessly coupling 1006 the first and second hearing devices, and activating 1008 a microphone and audio processing circuitry of the first hearing device. The Self-Check protocol 1004 also involves generating 1010 an acoustic test stimulus (e.g., a multiple-tone stimulus or a sweep-tone stimulus) using an acoustic transducer of the second hearing device. For example, the acoustic test stimulus can comprise a continuous sweep tone that sweeps a frequency range of about 100 Hz to about 10 kHz. The response to the microphone can be compared to a pre-established profile (e.g., a frequency response curve, a tuning curve) representative of nominal microphone performance. A specified deviation from the pre-established profile can be indicative of sub-optimal microphone performance. The specified deviation can be a specified number of decibels indicative of sub-optimal microphone performance (e.g., on a per sub-band basis) or a specified percentage drop in microphone performance, for example. The method shown in FIG. 10 also involves storing 1014 results of the performance assessment in the local memory. The method may also involve communicating 1016 the results from the local memory to a memory of an external electronic device or system (e.g., a smartphone, table, wireless access point, the cloud).

Figure 11:
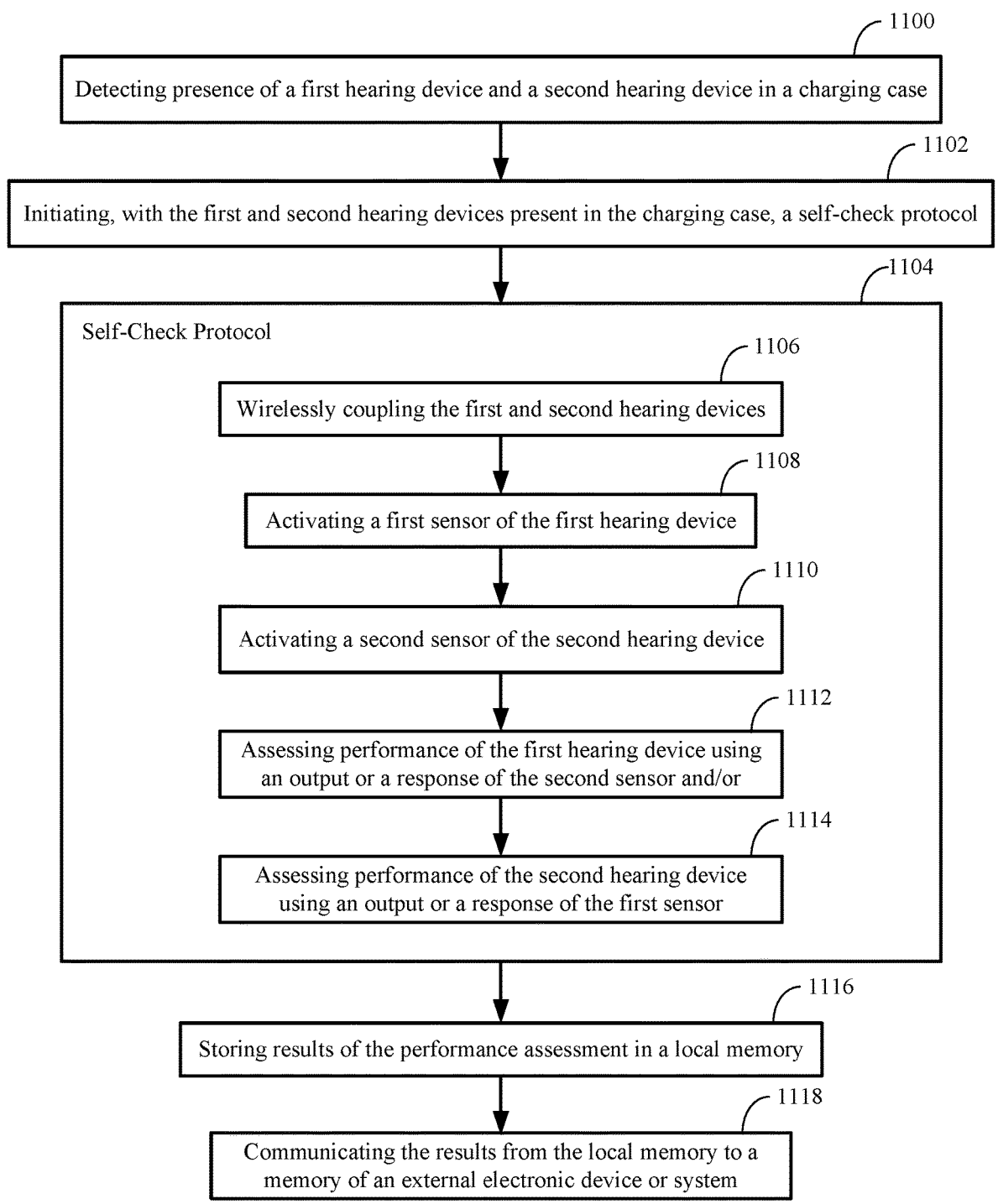
FIG. 11 illustrates a Self-Check protocol in accordance with any of the embodiments disclosed herein.

FIG. 11 illustrates a Self-Check protocol in accordance with any of the embodiments disclosed herein. The method shown in FIG. 11 involves detecting 1100 presence of a first hearing device and a second hearing device in a charging case. The method involves initiating 1102, with the first and second hearing devices present in the charging case, a Self-Check protocol 1104. The Self-Check protocol 1104 involves wirelessly coupling 1106 the first and second hearing devices, activating 1108 a first sensor of the first hearing device, and activating 1110 a second sensor of the second hearing device. The first and second sensors can be the same sensor or different sensors, such as any of the sensors disclosed herein. The Self-Check protocol 1104 also involves assessing 1112 performance of the first hearing device using an output or a response of the second sensor and/or assessing 1114 performance of the second hearing device using an output or a response of the first sensor.

In some implementations, the Self-Check protocol 1104 can involve calibrating one of more sensors of the first hearing device using an output or a response of one or more sensors of the second hearing device (and vice versa). For example, a check can be made on the motion sensor (e.g., IMU) calibration and offset. When the devices 100 are placed in the charging case 300, the standard use orientation of the charging case 300 will establish a known and referenceable orientation for the IMU and the calibration can be checked. The IMUS of the two devices 100 can cross-reference each other to verify what orientation the charging case 300 is in prior to adjusting any calibration in the event that the charging case 300 is not in the normal use case orientation. The method shown in FIG. 11 involves storing 1116 results of the performance assessment in the local memory. The method may also involve communicating 1118 the results from the local memory to a memory of an external electronic device or system (e.g., a smartphone, table, wireless access point, the cloud).

Figure 12:
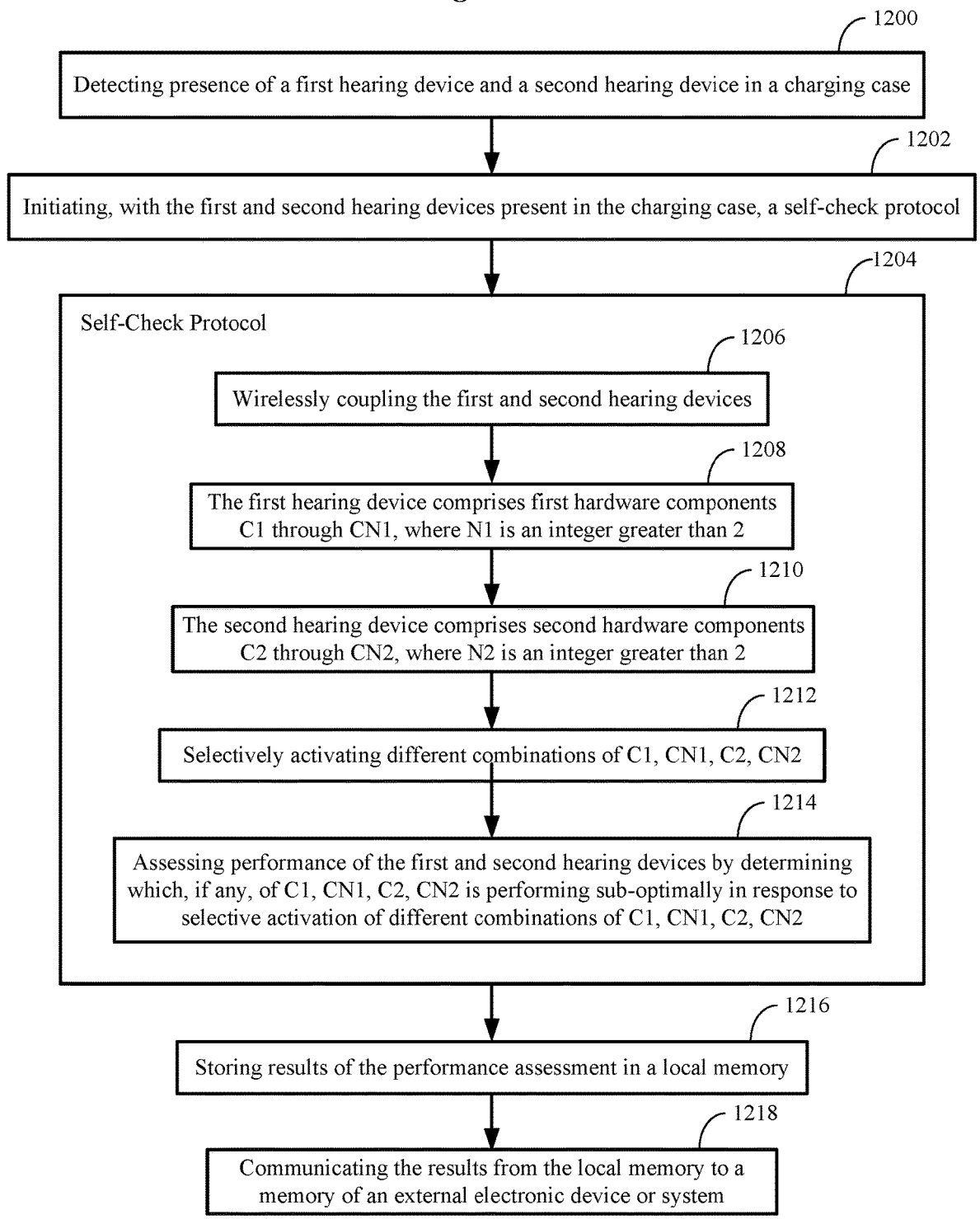
FIG. 12 illustrates a Self-Check protocol in accordance with any of the embodiments disclosed herein.

FIG. 12 illustrates a Self-Check protocol in accordance with any of the embodiments disclosed herein. The method shown in FIG. 12 involves detecting 1200 presence of a first hearing device and a second hearing device in a charging case. The method involves initiating 1202, with the first and second hearing devices present in the charging case, a Self-Check protocol 1204. The Self-Check protocol 1204 involves wirelessly coupling 1206 the first and second hearing devices. The first hearing device comprises 1208 first hardware components C1 through CN1, where N1 is an integer greater than 2. The second hearing device comprises 1210 second hardware components C2 through CN2, where N2 is an integer greater than 2.

The Self-Check protocol 1204 involves selectively activating different combinations of C1, CN1, C2, and CN2. The Self-Check protocol 1204 also involves assessing 1214 performance of the first and second hearing devices by determining which, if any, of C1, CN1, C2, and CN2 is performing sub-optimally in response to selective activation of different combinations of C1, CN1, C2, and CN2. In some implementations, the Self-Check protocol 1204 can involve calibrating one of more of the first hardware components C1-CN1 using an output or a response of one or more of the second hardware components C2-CN2 (and vice versa).

The method shown in FIG. 12 involves storing 1216 results of the performance assessment in the local memory. The method may also involve communicating 1218 the results stored in local memory to an external electronic device or system (e.g., a smartphone, table, wireless access point, the cloud). The hardware component or components subject to testing can be the same or different components, and can be any hearing device component disclosed herein. The hardware component or components can be, or include, electrical circuitry (e.g., a rigid or flexible PCB) which can be subject to a performance assessment via the Self-Check protocol 1204.

Figure 13:
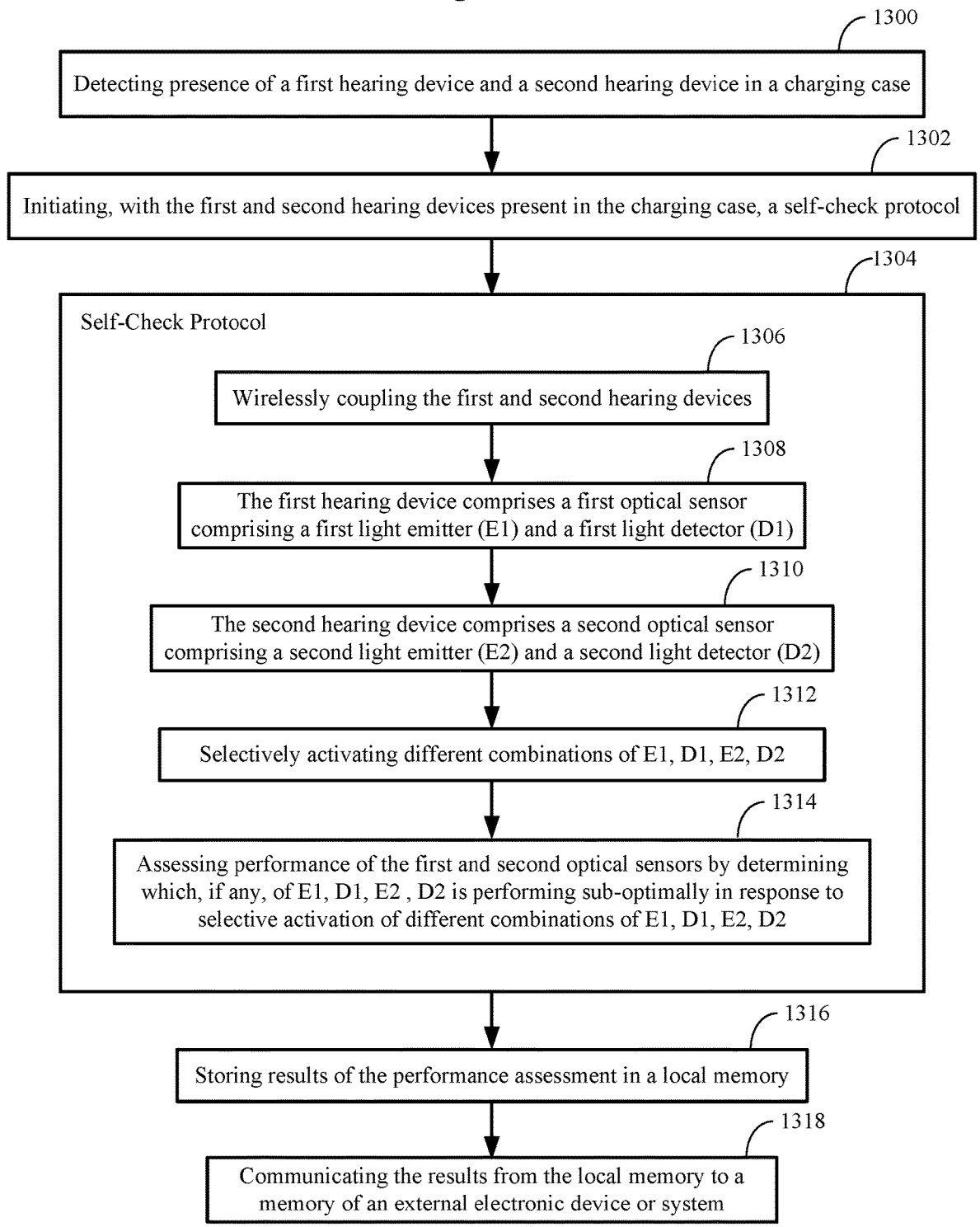
FIG. 13 illustrates a Self-Check protocol in accordance with any of the embodiments disclosed herein.

FIG. 13 illustrates a Self-Check protocol in accordance with any of the embodiments disclosed herein. The method shown in FIG. 13 involves detecting 1300 presence of a first hearing device and a second hearing device in a charging case. The method involves initiating 1302, with the first and second hearing devices present in the charging case, a Self-Check protocol 1304. The Self-Check protocol 1304 involves wirelessly coupling 1306 the first and second hearing devices. The first hearing device comprises 1308 a first optical sensor comprising a first light emitter, E1, and a first light detector, D1. The second hearing device comprises 1310 a second optical sensor comprising a second light emitter, E2, and a second light detector, D2. The first and second optical sensors can be PPG sensors, for example.

The Self-Check protocol 1304 involves selectively activating different combinations of E1, D1, E2, and D2. The Self-Check protocol 1304 also involves assessing 1314 performance of the first and second optical sensors by determining which, if any, of E1, D1, E2, and D2 is performing nominally or sub-optimally in response to selective activation of different combinations of E1, D1, E2, and D2. In some implementations, the Self-Check protocol 1304 can involve calibrating the first optical sensor using light produced by the second optical sensor, and calibrating the second optical sensor using light produced by the first optical sensor. The method shown in FIG. 13 involves storing 1316 results of the performance assessment in local memory. The method may also involve communicating 1318 the results from local memory to an external electronic device or system (e.g., a smartphone, table, wireless access point, the cloud).

Figure 14:
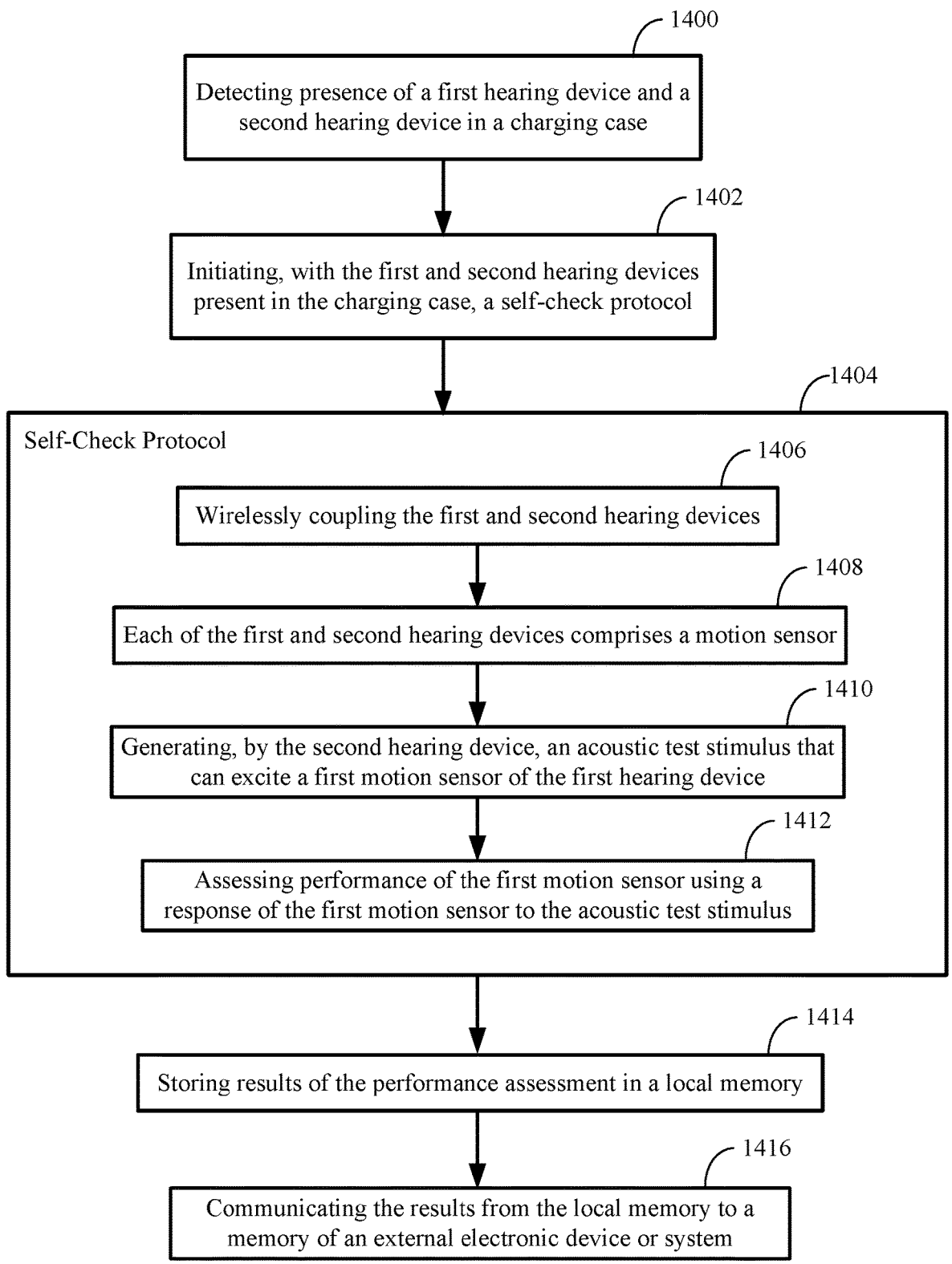
FIG. 14 illustrates a Self-Check protocol in accordance with any of the embodiments disclosed herein.

FIG. 14 illustrates a Self-Check protocol in accordance with any of the embodiments disclosed herein. The method shown in FIG. 14 involves detecting 1400 presence of a first hearing device and a second hearing device in a charging case. The method involves initiating 1402, with the first and second hearing devices present in the charging case, a Self-Check protocol 1404. The Self-Check protocol 1404 involves wirelessly coupling 1406 the first and second hearing devices. Each of the first and second hearing devices comprises 1408 a motion sensor. The Self-Check protocol 1404 involves generating 1410, by the second hearing device, and acoustic test stimulus that can excite a first motion sensor of the first hearing device. The Self-Check protocol 1404 also involves assessing 1412 performance of the first motion sensor using a response of the first motion sensor to the acoustic test stimulus. The Self-Check protocol 1404 is repeated to assess the performance of a second motion sensor of the second hearing device (e.g., in response to an acoustic test stimulus generated by the first hearing device which can excite the second motion sensor of the second hearing device). The method shown in FIG. 14 also involves storing 1414 results of the performance assessment in local memory. The method may also involve communicating 1416 the results from the local memory to an external electronic device or system (e.g., a smartphone, table, wireless access point, the cloud).

Figure 15:
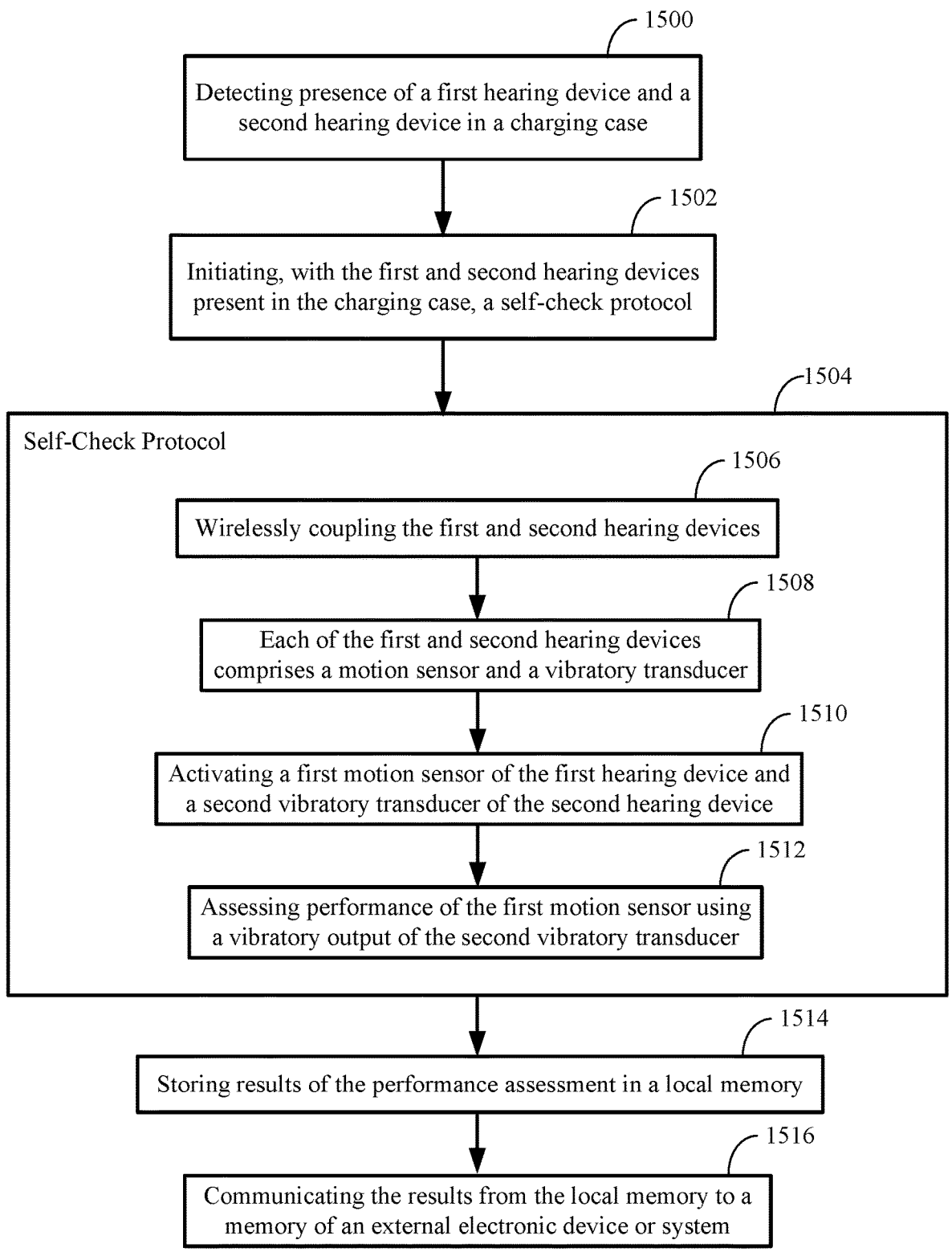
FIG. 15 illustrates a Self-Check protocol in accordance with any of the embodiments disclosed herein.

FIG. 15 illustrates a Self-Check protocol in accordance with any of the embodiments disclosed herein. The method shown in FIG. 15 involves detecting 1500 presence of a first hearing device and a second hearing device in a charging case. The method involves initiating 1502, with the first and second hearing devices present in the charging case, a Self-Check protocol 1504. The Self-Check protocol 1504 involves wirelessly coupling 1506 the first and second hearing devices. Each of the first and second hearing devices comprises 1508 a motion sensor and a vibratory transducer. The Self-Check protocol 1504 involves activating 1510 a first motion sensor of the first hearing device and a second vibratory transducer of the second hearing device. The Self-Check protocol 1504 involves assessing 1512 performance of the first motion sensor using a vibratory output of the second vibratory transducer. The Self-Check protocol 1504 is repeated to assess performance of a second motion sensor of the second hearing device using a vibratory output of a first vibratory transducer of the first hearing device. The method shown in FIG. 15 also involves storing 1514 results of the performance assessment in local memory. The method may also involve communicating 1516 the results from local memory to an external electronic device or system (e.g., a smartphone, table, wireless access point, the cloud).

Figure 16:
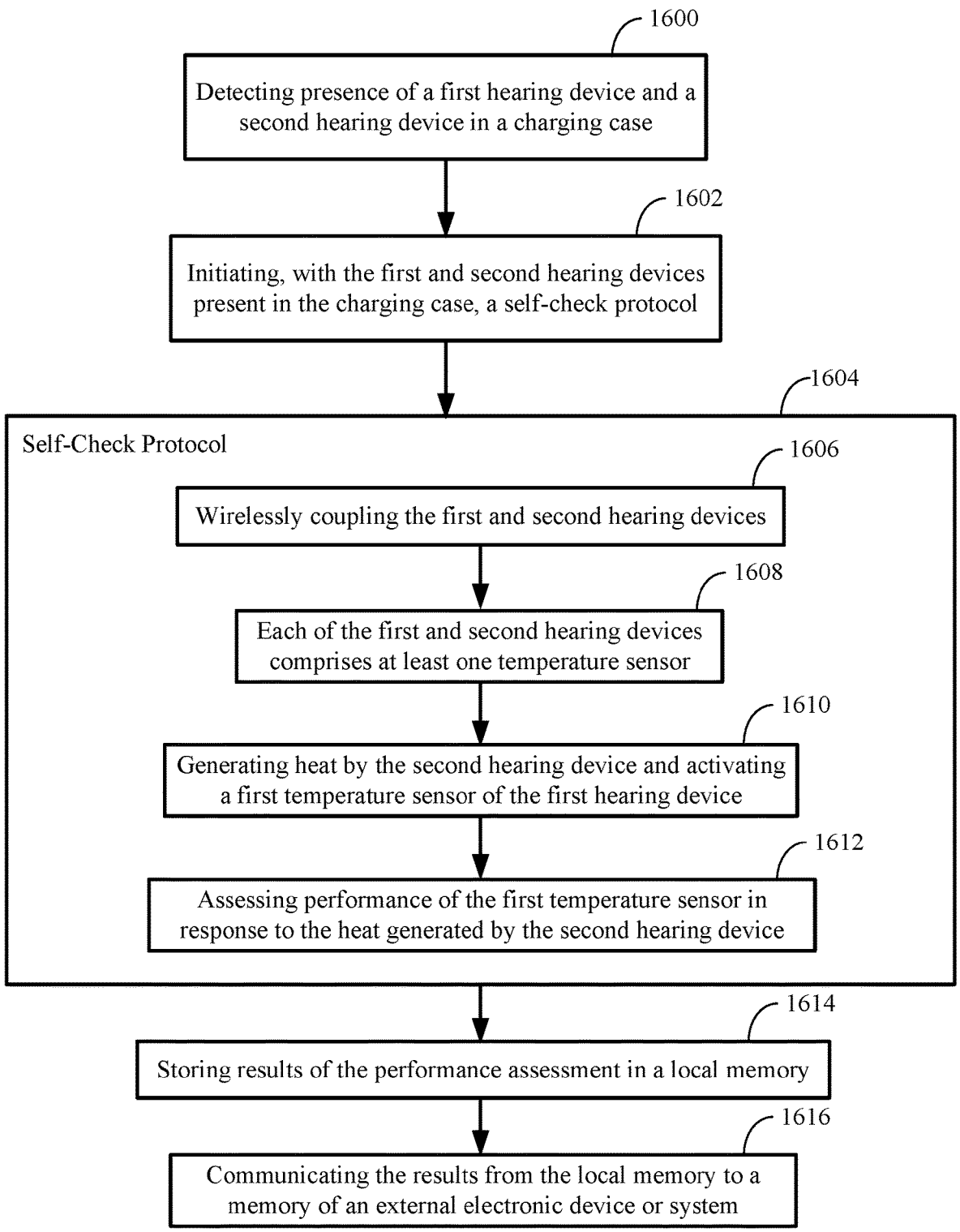
FIG. 16 illustrates a Self-Check protocol in accordance with any of the embodiments disclosed herein.

FIG. 16 illustrates a Self-Check protocol in accordance with any of the embodiments disclosed herein. The method shown in FIG. 16 involves detecting 1600 presence of a first hearing device and a second hearing device in a charging case. The method involves initiating 1602, with the first and second hearing devices present in the charging case, a Self-Check protocol 1604. The Self-Check protocol 1604 involves wirelessly coupling 1606 the first and second hearing devices. Each of the first and second hearing devices comprises at least one temperature sensor. The Self-Check protocol 1604 involves generating 1610 heat by the second hearing device, and activating a first temperature sensor of the first hearing device. The Self-Check protocol 1604 also involves assessing 1612 performance of the first temperature sensor in response to the heat generated by the second hearing device. The Self-Check protocol 1604 is repeated by generating heat by the first hearing device, activating a second temperature sensor of the second hearing device, and assessing performance of the second temperature sensor in response to the heat generated by the first hearing device. The first and second temperature sensors can also be calibrated using heat generated from the other hearing device and a pre-established temperature profile indicative of a nominal temperature sensor response.

The heat produced by the first and second hearing devices can be generated by charging (e.g., overcharging depending on the depth of charge) one of the first and second hearing devices while not subjecting the other of the first and second hearing devices to charging. The Self-Check protocol 1604 can also involve calibrating the first and second temperature sensors after expiration of a predetermined time period (e.g., 30-60 minutes) after detecting closure of the charging case lid, such that the acoustic chamber within the charging case reaches stead-state or near steady-state temperature. The method shown in FIG. 16 also involves storing 1614 results of the performance assessment in local memory. The method may also involve communicating 1616 the results from the local memory to an external electronic device or system (e.g., a smartphone, table, wireless access point, the cloud).

Figure 17:
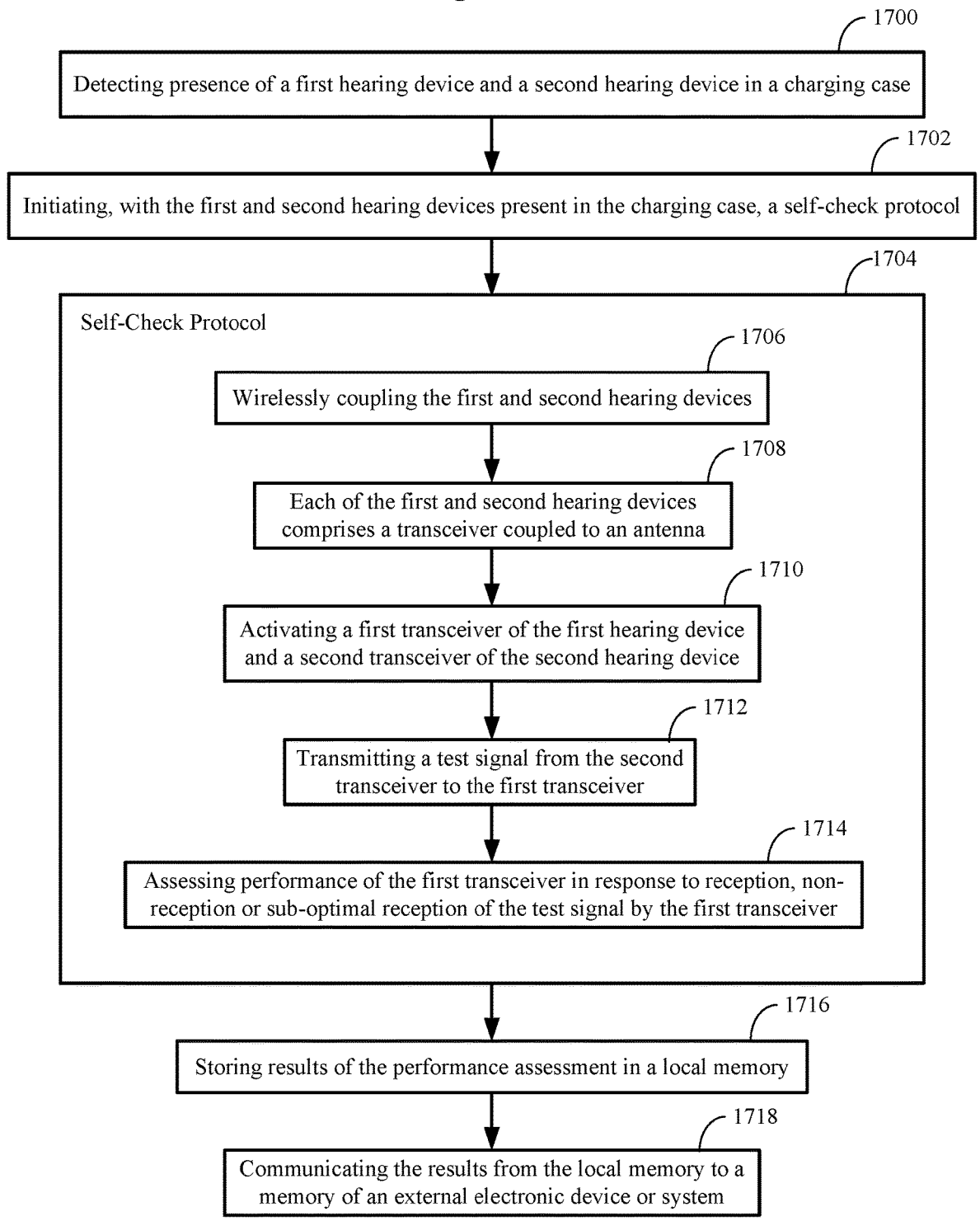
FIG. 17 illustrates a Self-Check protocol in accordance with any of the embodiments disclosed herein.

FIG. 17 illustrates a Self-Check protocol in accordance with any of the embodiments disclosed herein. The method shown in FIG. 17 involves detecting 1700 presence of a first hearing device and a second hearing device in a charging case. The method involves initiating 1702, with the first and second hearing devices present in the charging case, a Self-Check protocol 1704. The Self-Check protocol 1704 involves wirelessly coupling 1706 the first and second hearing devices. Each of the first and second hearing devices comprises an RF transceiver coupled to an antenna. The Self-Check protocol 1704 involves activating 1710 a first transceiver of the first hearing device and a second transceiver of the second hearing device. The Self-Check protocol 1704 involves transmitting 1712 a test signal from the second transceiver to the first transceiver, and assessing 1714 performance of the first transceiver in response to reception, non-reception or sub-optimal reception of the test signal by the first transceiver. The Self-Check protocol 1704 is repeated by transmitting a test signal from the first transceiver to the second transceiver, and assessing performance of the second transceiver in response to reception, non-reception, or sub-optimal reception of the test signal by the second transceiver. The method shown in FIG. 17 involves storing 1716 results of the performance assessment in local memory. The method may also involve communicating 1718 the results from the local memory to an external electronic device or system (e.g., a smartphone, table, wireless access point, the cloud).

Figure 18:
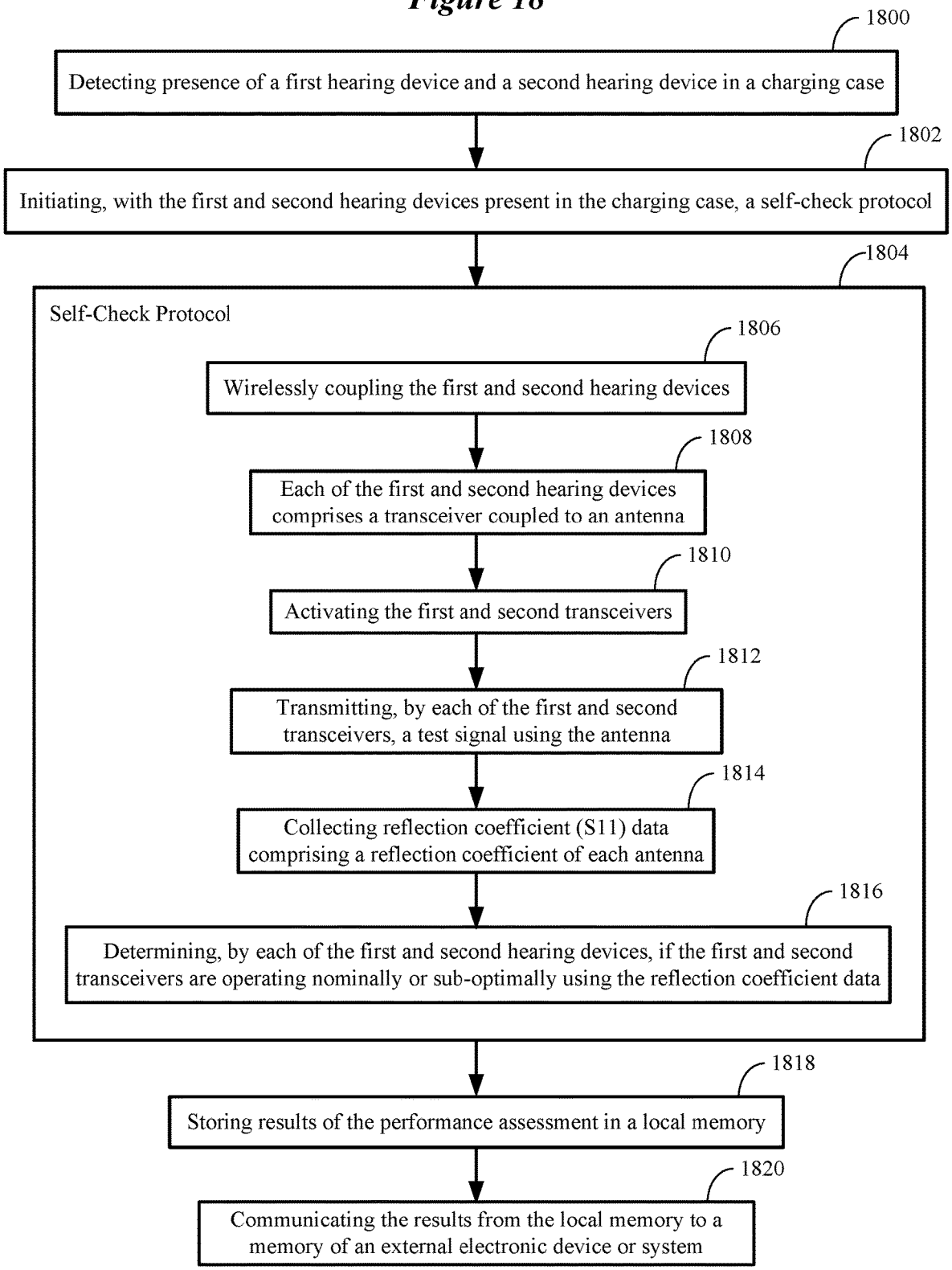
FIG. 18 illustrates a Self-Check protocol in accordance with any of the embodiments disclosed herein.

FIG. 18 illustrates a Self-Check protocol in accordance with any of the embodiments disclosed herein. The method shown in FIG. 18 involves detecting 1800 presence of a first hearing device and a second hearing device in a charging case. The method involves initiating 1802, with the first and second hearing devices present in the charging case, a Self-Check protocol 1804. The Self-Check protocol 1804 involves wirelessly coupling 1806 the first and second hearing devices. Each of the first and second hearing devices comprises 1808 an RF transceiver coupled to an antenna. The Self-Check protocol 1804 involves transmitting 1812, by each of the first and second transceivers, a test signal using their respective antenna. The Self-Check protocol 1804 also involves collecting 1814 reflection coefficient (S11) data comprising a reflection coefficient of each antenna. The Self-Check protocol 1804 further involves determining 1816, by each of the first and second hearing devices, if the first and second transceivers are operating nominally or sub-optimally using the reflection coefficient data. The method shown in FIG. 18 involves storing 1818 results of the performance assessment in local memory. The method may also involve communicating 1820 the results from the local memory to an external electronic device or system (e.g., a smartphone, table, wireless access point, the cloud).

Figure 19:
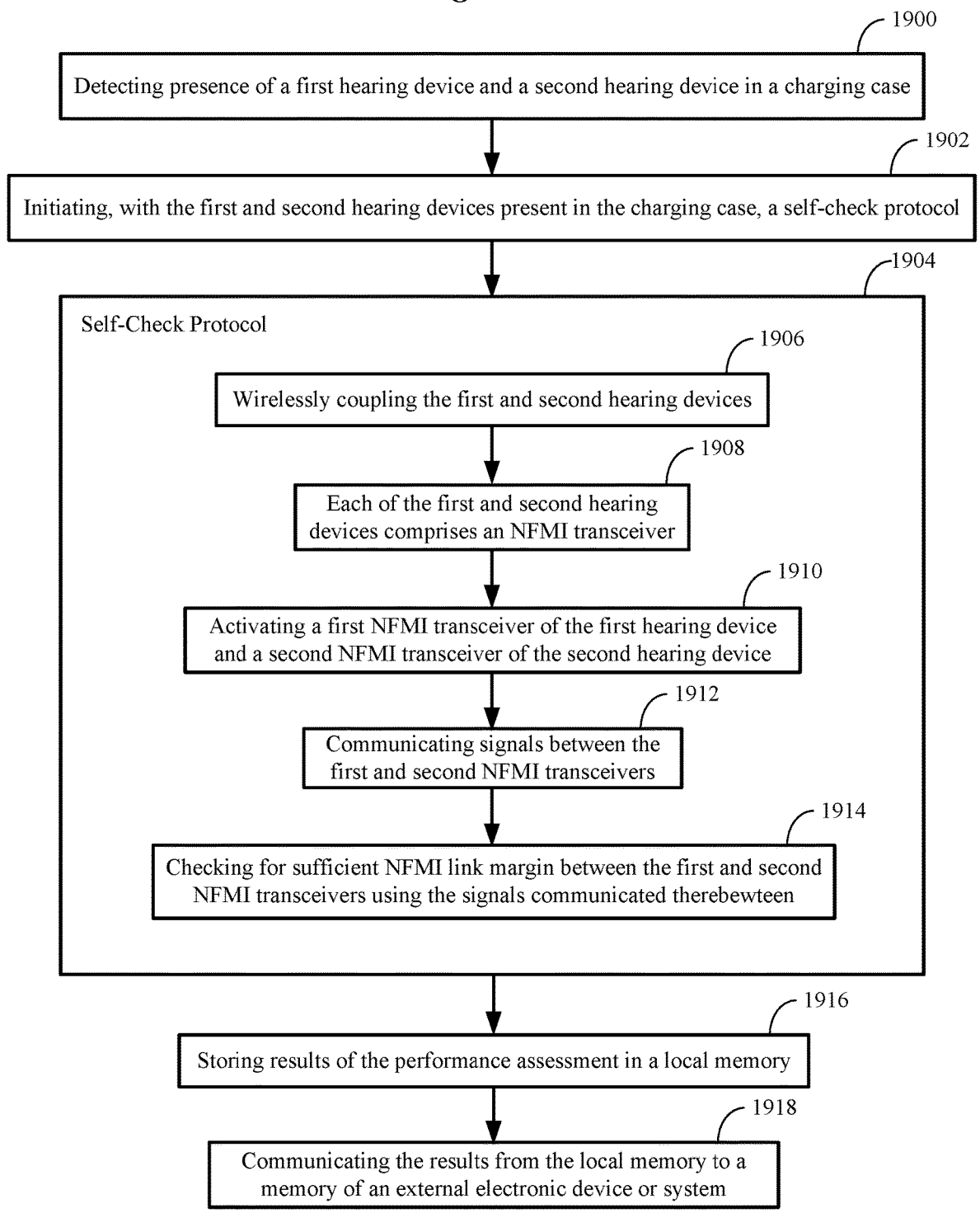
FIG. 19 illustrates a Self-Check protocol in accordance with any of the embodiments disclosed herein.

FIG. 19 illustrates a Self-Check protocol in accordance with any of the embodiments disclosed herein. The method shown in FIG. 19 involves detecting 1900 presence of a first hearing device and a second hearing device in a charging case. The method involves initiating 1902, with the first and second hearing devices present in the charging case, a Self-Check protocol 1904. The Self-Check protocol 1904 involves wirelessly coupling 1906 the first and second hearing devices. Each of the first and second hearing devices comprises 1908 and an NFMI transceiver. The Self-Check protocol 1904 involves communicating 1912 signals between the first and second NFMI transceivers. The Self-Check protocol 1904 also involves checking 1914 for sufficient NFMI link margin between the first and second NFMI transceivers using the signals communicated therebetween. The method shown in FIG. 19 involves storing 1916 results of the performance assessment in the local memory. The method may also involve communicating 1918 the results from the local memory to a memory of an external electronic device or system (e.g., a smartphone, table, wireless access point, the cloud).

FIG. 20 illustrates a Self-Check protocol in accordance with any of the embodiments disclosed herein. The method shown in FIG. 20 involves detecting 2000 presence of a first hearing device and a second hearing device in a charging case. The method involves initiating 2002, with the first and second hearing devices present in the charging case, a Self-Check protocol 2004. The Self-Check protocol 2004 involves wirelessly coupling 2006 the first and second hearing devices. Each of the first and second hearing devices comprises 2008 at least one electrode-based sensor. The Self-Check protocol 2004 involves generating 2010 a test signal by the second hearing device, and assessing 2012 performance of the first electrode-based sensor using the test signal received from the second hearing device by the first electrode-based sensor. The Self-Check protocol 2004 is repeated, which involves generating a test signal by the first hearing device, and assessing performance of the second electrode-based sensor using the test signal received from the first hearing device by the second electrode-based sensor. The method shown in FIG. 20 also involves storing 2014 results of the performance assessment in local memory. The method may also involve communicating 2020 the results from the local memory to an external electronic device or system (e.g., a smartphone, table, wireless access point, the cloud).

Referring again to FIG. 3, the following discussion is directed to assessing the viability of acoustic testing of hearing devices 100 within an enclosed acoustic chamber 315 in accordance with any of the embodiments disclosed herein. For purposes of the following discussion, the two hearing devices 100 shown in FIG. 3 will be referred to as a first hearing device (e.g., the left hearing device 100 shown in FIG. 3) and a second hearing device (e.g., the right hearing device 100 shown in FIG. 3). In general, the assessment seeks to determine if the microphone and/or receiver of the first and second hearing devices are operating optimally (e.g., within specification) or sub-optimally (e.g., out of specification, failing). In addition, the assessment seeks to determine whether the acoustic chamber 315 is performing properly for conducting an acoustic test of the first and second hearing devices or whether the conditions of the acoustic chamber 315 have deteriorated such that acoustic testing results are unreliable.

Initially, frequency response data is established for the first and second hearing devices either at the time of manufacture or during a fitting by an audiologist or hearing professional. This initial frequency response data is stored in the memory of one or both of the first and second hearing devices. Initial acoustic chamber response data can also established, typically at the time of manufacture, during a calibration process in which the first and second hearing devices are placed in a known ("good") firmware configuration and the frequency response is measured on both the first and second hearing devices. This initial ("good") acoustic chamber response data is stored in one or both of the first and second hearing devices (and/or in a memory of the charging case 300).

In some implementations, it may be useful to obtain frequency response data for the acoustic chamber 315 when the acoustic chamber 315 is not in a state that would provide reliable acoustic testing results. Initial sub-optimal acoustic chamber response data can be established, typically at the time of manufacture. In some implementations, profiles of different sub-optimal acoustic chamber response data can be established for different acoustic chamber conditions, such as in the case where the acoustic chamber 315 is open, the receiver of a hearing device is blocked, or an object is positioned within the acoustic chamber 315. These profiles of "bad" acoustic chamber response data can be stored in one or both of the first and second hearing devices (and/or in a memory of the charging case 300).

According to a representative acoustic testing procedure, the first hearing device generates an acoustic test stimulus (e.g., an impulse or frequency sweep) by its receiver which is received by the first hearing device's microphone to produce first frequency response data. Next, the second hearing device generates an acoustic test stimulus by its receiver which is received by the second hearing device's microphone to produce second frequency response data. The frequency response data can be in the form of the magnitude of energy of different bands (e.g., sub-bands) in the frequency response (e.g., via an FFT operation). Alternatively, the frequency response data can be in the form of magnitude of total energy in the frequency response (e.g., all bands).

Various comparison operations can be performed by one or both of the hearing devices using the frequency response data. In some implementations, the second frequency response data can be transferred from the second hearing device to the first hearing device, and the first hearing device can perform the comparison operations. In other implementations, and for certain comparison operations, each of the hearing devices can perform its own comparison operation.

A first comparison operation can be performed in which frequency response data is compared to previously established initial frequency response data for each of the first and second hearing devices. If a hearing device's test frequency response data is relatively the same as its initial frequency response data (e.g., a deviation of 5% or less), then it can be assumed that the hearing device is operating properly (e.g., within specification). If both hearing devices are found to be operating within specification, then it can also be assumed that the environment of the acoustic chamber 315 has not deteriorated. If a hearing device's frequency response data deviates from its initial frequency response data by more than a specified value or threshold (e.g., >5% deviation), then it can be assumed that the hearing device is operating sub-optimally (e.g., failing) or the environment of the acoustic chamber 315 has deteriorated.

When the environment of the acoustic chamber 315 has deteriorated, it is expected that the frequency response of both the first and second devices differ from that indicated by their initial frequency response data. In this case, it can be assumed that either both the first and second devices are failing or the environment of the acoustic chamber 315 has deteriorated. The frequency response data of one or both of the first and second devices can be compared to the profiles of "bad" acoustic chamber response data. If the frequency response data of one or both of the first and second devices matches one of the profiles, then it can be assumed that the environment of the acoustic chamber 315 has deteriorated. If it is determined that the acoustic chamber environment has not deteriorated, then one of both of the first and second devices are failing and additional testing can be performed as discussed below.

A second comparison operation can be performed in which the second frequency response data of the second hearing device is transferred to the first hearing device. The first hearing device can compare the first frequency response data to the second frequency response data. If the comparison reveals that the first and second frequency response data are relatively similar (e.g., within a deviation of 5%), then it can be assumed that the acoustic chamber environment is good. If the comparison reveals that the first and second frequency response data are dissimilar, then either one or both of the hearing devices are failing or the environment of the acoustic chamber 315 has deteriorated. The frequency response data of one or both of the first and second devices can be compared to the profiles of "bad" acoustic chamber response data to determine if the environment of the acoustic chamber 315 has deteriorated. If it is determined that the acoustic chamber environment has not deteriorated, then one of both of the first and second devices are failing and additional testing can be performed as discussed below.

When it is determined that a hearing device is operating sub-optimally, additional testing can be performed to determine if the problem is a defective microphone or a defective receiver. The first and second hearing devices can cooperate to test the performance of the microphones and receivers of the two devices in a systematic manner to identify which component is performing sub-optimally. In the following example, it is assumed that the frequency response data for the first hearing device is out of specification, and that the frequency response data for the second device is within specification. For simplicity, the microphones of the first and second hearing devices are referred to as M1 and M2, and the receivers of the first and second hearing devices are referred to as R1 and R2.

Assuming M2 and R2 are within specification, R2 emits an acoustic test stimulus which is sensed by M1. Frequency response data is computed for M1 and compared to initial frequency response data for the first hearing device. In this example, the comparison indicates that M1 is within specification. R1 emits an acoustic test stimulus which is sensed by M1. Frequency response data is computed for M1 and compared to initial frequency response data for the first hearing device. In this example, the computed frequency response data does not match with the initial frequency response data for the first hearing device. The result of the acoustic test indicates that R1 is out of specification. It can be appreciated that variations of this testing approach can be implemented to assess the operational status of M1, R1, M2, and R2.

Additional processes can be implemented by a hearing device 100 to correct the frequency response of the hearing device 100 in accordance with any of the embodiments disclosed herein. In this illustrative example, it is assumed that the frequency response of the hearing device 100 has been determined to be out of specification, as opposed to the acoustic chamber 315. More particularly, it is assumed that the microphone response has been determined to be out of specification using an acoustic testing procedure previously described. In this example, the hearing device 100 stores a hearing device response curve (e.g., a tuning curve) that has had a user's audiogram applied to it.

The hearing device 100 can be configured to determine a correction factor on a per-sub-band basis using the hearing device response curve to bring the frequency response back into specification. For example, gain or attenuation can be applied per band until the frequency response is adjusted to within tolerance indicated by the hearing device response curve. For example, acoustic testing of the hearing device 100 may have revealed that the gain within the 5K-6K frequency range is off by 3 dB. An offset indicated by the hearing device response curve can be applied by the sub-band gain processor of the hearing device 100 to bring the frequency response back into specification.

At this point, the correction made to bring the frequency response back into specification is saved in the hearing device memory and can be sent from the hearing device to the manufacturer for assessment (e.g., wirelessly via the internet or via the charging case 300). Based on the correction required as compared to a baseline, the manufacturer may flag this corrected hearing device as a quality risk. This can trigger a call, an email or a mobile app notification from a customer service representative or automated cloud based system to either the wearer of the hearing device 100 or hearing professional in order to proceed with further servicing steps such as cleaning, receiver cable replacement, or further device repair.

Referring again to the block diagrams shown in FIGS. 2A, 3, and 4, the controller 120 can include one or more processors or other logic devices. For example, the controller 120 can be representative of any combination of one or more logic devices (e.g., multi-core processor, digital signal processor (DSP), microprocessor, programmable controller, general-purpose processor, special-purpose processor, hardware controller, software controller, a combined hardware and software device) and/or other digital logic circuitry (e.g., ASICs, FPGAs), and software/firmware configured to implement the functionality disclosed herein (e.g., implementing a Self-Check protocol). The controller 120 can incorporate or be coupled to various analog components (e.g., analog front-end), ADC and DAC components, and Filters (e.g., FIR filter, Kalman filter). The memory 122 can include one or more types of memory, including ROM, RAM, SDRAM, NVRAM, EEPROM, and FLASH, for example. The controller 120 can be coupled to, or incorporate, the memory 122.

Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety into this disclosure, except to the extent they may directly contradict this disclosure. Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a radio chip may be operably coupled to an antenna element to provide a radio frequency electric signal for wireless communication).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like. The term "and/or" means one or all of the listed elements or a combination of at least two of the listed elements.

The phrases "at least one of," "comprises at least one of," and "one or more of" followed by a list refers to any one of the items in the list and any combination of two or more items in the list.

What is claimed is:

1. A method, comprising:
    initiating, with first and second hearing devices present in a charging case, a self-check protocol by at least one of the first and second hearing devices, the self-check protocol comprising:
        wirelessly coupling the first and second hearing devices;
        activating a first microphone of the first hearing device and generating an acoustic test stimulus by a second acoustic transducer of the second hearing device;
        assessing performance of the first microphone in response to the acoustic test stimulus by:
            comparing a response of the first microphone to a pre-established profile representative of nominal microphone performance; and
            detecting sub-optimal performance of the first microphone in response to measuring a specified deviation from the pre-established profile;
        activating a second microphone of the second hearing device and generating an acoustic test stimulus by a first acoustic transducer of the first hearing device;
        assessing performance of the second microphone in response to the acoustic test stimulus by:
            comparing a response of the second microphone to the pre-established profile; and
            detecting sub-optimal performance of the second microphone in response to measuring a specified deviation from the pre-established profile; and
        storing results of the performance assessment in a memory;
    wherein the self-check protocol is repeated over time, and the method further comprises:
        tracking changes in performance of the first and second microphones over time; and
        determining or predicting when performance of the first or second microphone becomes sub-optimal using the tracked performance changes.

2. The method of claim 1, wherein the acoustic test stimulus comprises a multi-tone signal.

3. The method of claim 1, wherein the acoustic test stimulus comprises a continuous sweep tone.

4. The method of claim 1, wherein the acoustic test stimulus comprises a continuous sweep tone that sweeps a frequency range of about 100 Hz to about 10 kHz.

5. The method of claim 1, further comprising:
    activating a first component of the first hearing device and a second component of the second hearing device;
    assessing performance of the first hearing device using an output or a response of the second component; and
    assessing performance of the second hearing device using an output or a response of the first component.

6. The method of claim 1, further comprising:
    activating a first sensor of the first hearing device and a second sensor of the second hearing device; and
    assessing performance of one of both of:
        the first hearing device using an output or a response of the second sensor; and
        the second hearing device using an output or a response of the first sensor;
    wherein the first sensor and the second sensor comprise one or more of an electrode-based sensor, an optical physiologic sensor, a temperature sensor, a motion sensor, and a biochemical sensor.

7. The method of claim 1, wherein the first hearing device comprises a first sensor and the second hearing device comprises a second sensor, and the method further comprises:
    activating the first sensor and one or both of the second sensor and a second electronic component of the second hearing device;
    activating the second sensor and one or both of the first sensor and a first electronic component of the second hearing device;
    assessing performance of the first hearing device using an output or a response of one or both of the second sensor and the second electronic component; and
    assessing performance of the second hearing device using an output or a response of one or both of the first component and the first electronic component;
    wherein the first sensor and the second sensor comprise one or more of an electrode-based sensor, an optical physiologic sensor, a temperature sensor, a motion sensor, and a biochemical sensor.

8. The method of claim 1, wherein:
    the first hearing device comprises a first optical sensor and the second hearing device comprises a second optical sensor;
    the first optical sensor comprises a first light emitter (E1) and a first light detector (D1);
    the second optical sensor comprises a second light emitter (E2) and a second light detector (D2); and
    the method further comprises
        selectively activating different combinations of E1, D1, E2, D2; and
        assessing performance of the first and second optical sensors by determining which, if any, of E1, D1, E2, D2 is performing sub-optimally in response to selective activation of different combinations of E1, D1, E2, D2.

9. The method of claim 8, wherein the first and second optical sensors comprise one or more of a PPG sensor, a pulse oximeter, a blood oxygen (SpO$_2$) sensor, a heart rate sensor, and a respiration sensor.

10. The method of claim 8, comprising:
calibrating the first optical sensor using light produced by the second optical sensor; and
calibrating the second optical sensor using light produced by the first optical sensor.

11. The method of claim 1, wherein each of the first and second hearing devices comprises a motion sensor, and the method further comprises:
generating, by the second hearing device, an acoustic test stimulus or vibratory output that can excite a first motion sensor of the first hearing device; and
assessing performance of the first motion sensor using a response of the first motion sensor to the acoustic test stimulus or the vibratory output.

12. The method of claim 1, wherein each of the first and second hearing devices comprises at least one temperature sensor, and the method further comprises:
generating heat by the second hearing device in response to charging and activating a first temperature sensor of the first hearing device; and
assessing performance of the first temperature sensor in response to the heat generated by the second hearing device.

13. The method of claim 12, comprising calibrating the at least one temperature sensor after expiration of a predetermined time period after detecting closure of a charging case lid.

14. The method of claim 1, wherein each of the first and second hearing devices comprises a transceiver coupled to an antenna, and the method further comprises:
activating a first transceiver of the first hearing device and a second transceiver of the second hearing device;
transmitting a test signal from the second transceiver to the first transceiver; and
assessing performance of the first transceiver in response to reception or non-reception of the test signal by the first transceiver.

15. The method of claim 1, wherein each of the first and second hearing devices comprises a transceiver coupled to an antenna, and the method further comprises:
assessing, by each of the first and second hearing devices, transceiver and antenna performance by:
transmitting a test signal using the antenna;
collecting reflection coefficient (S11) data comprising a reflection coefficient of the antenna; and
determining, by each of the first and second hearing devices, if the first and second transceivers are operating sub-optimally using the reflection coefficient data.

16. The method of claim 1, wherein each of the first and second hearing devices comprises an NFMI transceiver, and the method further comprises:
activating a first NFMI transceiver of the first hearing device and a second NFMI transceiver of the second hearing device;
communicating signals between the first and second NFMI transceivers; and
checking for sufficient NFMI link margin between the first and second NFMI transceivers using the signals communicated therebetween.

17. Ear-wearable electronic devices configured to facilitate performance of a self-check protocol within a charging case, the devices comprising:
a first hearing device and a second hearing device each comprising a microphone, an acoustic transducer, a communication device, and a controller coupled to memory, the controller of at least one of the first and second hearing devices configured to:
activate a first microphone of the first hearing device and generate an acoustic test stimulus by a second acoustic transducer of the second hearing device;
assess performance of the first microphone in response to the acoustic test stimulus by:
comparing a response of the first microphone to a pre-established profile representative of nominal microphone performance; and
detecting sub-optimal performance of the first microphone in response to measuring a specified deviation from the pre-established profile;
activate a second microphone of the second hearing device and generate an acoustic test stimulus by a first acoustic transducer of the first hearing device; and
assess performance of the second microphone in response to the acoustic test stimulus by:
comparing a response of the second microphone to the pre-established profile; and
detecting sub-optimal performance of the second microphone in response to measuring a specified deviation from the pre-established profile; and
store results of the performance assessment in a memory;
wherein the self-check protocol is repeated over time, and the controller is configured to:
track changes in performance of the first and second microphones over time; and
determine or predict when performance of the first or second microphone becomes sub-optimal using the tracked performance changes.

18. The devices of claim 17, wherein the acoustic test stimulus comprises a multi-tone signal or a continuous sweep tone.

19. The devices of claim 17, wherein:
the first hearing device comprises a first optical sensor and the second hearing device comprises a second optical sensor;
the first optical sensor comprises a first light emitter (E1) and a first light detector (D1);
the second optical sensor comprises a second light emitter (E2) and a second light detector (D2); and
the controller is configured to:
selectively activate different combinations of E1, D1, E2, D2; and
assess performance of the first and second optical sensors by determining which,
if any, of E1, D1, E2, D2 is performing sub-optimally in response to selective activation of different combinations of E1, D1, E2, D2.

20. The devices of claim 17, wherein each of the first and second hearing devices comprises a motion sensor, and the controller is configured to:
generate, by the second hearing device, an acoustic test stimulus or vibratory output that can excite a first motion sensor of the first hearing device; and
assess performance of the first motion sensor using a response of the first motion sensor to the acoustic test stimulus or the vibratory output.

21. The devices of claim 17, wherein each of the first and second hearing devices comprises at least one temperature sensor, and the controller is configured to:

cause heat generation by the second hearing device in response to charging and activate a first temperature sensor of the first hearing device; and assessing performance of the first temperature sensor in response to the heat generated by the second hearing device.

22. The devices of claim 17, wherein each of the first and second hearing devices comprises a transceiver coupled to an antenna, and the controller is configured to:

activate a first transceiver of the first hearing device and a second transceiver of the second hearing device;

transmit a test signal from the second transceiver to the first transceiver; and assess performance of the first transceiver in response to reception or non-reception of the test signal by the first transceiver.

23. The devices of claim 17, wherein each of the first and second hearing devices comprises a transceiver coupled to an antenna, and the controller is configured to assess transceiver and antenna performance of each of the first and second hearing devices by:

transmitting a test signal using the antenna;

collecting reflection coefficient (S11) data comprising a reflection coefficient of the antenna; and determining if the first and second transceivers are operating sub-optimally using the reflection coefficient data.

24. The devices of to claim 17, wherein each of the first and second hearing devices comprises an NFMI transceiver, and the controller is configured to:

activate a first NFMI transceiver of the first hearing device and a second NFMI transceiver of the second hearing device;

communicate signals between the first and second NFMI transceivers; and check for sufficient NFMI link margin between the first and second NFMI transceivers using the signals communicated therebetween.

* * * * *